(12) United States Patent
Rosenberger

(10) Patent No.: US 12,425,117 B2
(45) Date of Patent: Sep. 23, 2025

(54) TESTING OF A PRELIMINARY FILM PRODUCT

(71) Applicant: MALAO GMBH, Munich (DE)

(72) Inventor: Matthias Rosenberger, Miesbach (DE)

(73) Assignee: MALAO GMBH, Munich (DE)

( * ) Notice: Subject to any disclaimer, the term of this patent is extended or adjusted under 35 U.S.C. 154(b) by 212 days.

(21) Appl. No.: 18/041,676

(22) PCT Filed: Sep. 2, 2021

(86) PCT No.: PCT/EP2021/074311
§ 371 (c)(1),
(2) Date: Feb. 14, 2023

(87) PCT Pub. No.: WO2022/053399
PCT Pub. Date: Mar. 17, 2022

(65) Prior Publication Data
US 2023/0297925 A1    Sep. 21, 2023

(30) Foreign Application Priority Data
Sep. 2, 2020 (DE) ................ 10 2020 123 554.2

(51) Int. Cl.
*H04H 60/33* (2008.01)
*A61B 5/16* (2006.01)
(Continued)

(52) U.S. Cl.
CPC .............. *H04H 60/33* (2013.01); *A61B 5/16* (2013.01); *A61B 2503/12* (2013.01); *H04H 60/31* (2013.01); *H04N 21/4667* (2013.01)

(58) Field of Classification Search
CPC .......... H04H 60/33; H04H 60/31; A61B 5/16; A61B 2503/12; H04N 21/4667; G06Q 10/06395
See application file for complete search history.

(56) References Cited

U.S. PATENT DOCUMENTS 6,422,999 B1 * 7/2002 Hill ................. A61B 5/395
600/300
6,453,241 B1 * 9/2002 Bassett, Jr. ............ G16B 25/10
435/6.1

(Continued)

OTHER PUBLICATIONS

International Search Report issued in PCT/EP2021/074311; mailed Nov. 26, 2021.

*Primary Examiner* — Fernando Alcon
(74) *Attorney, Agent, or Firm* — Studebaker Brackett PLLC

(57) ABSTRACT

A method for testing a preliminary film product (FVP) is described. With the method a preliminary film product (FVP) is provided to a selected circle of test persons (8). During or immediately after receipt of the preliminary film product (FVP) by the test persons (8) reaction signals (E, ZS) are recorded section-wise by the test persons (8). The recorded reaction signals (E, ZS) are automatically evaluated for generating rating result data (BE) of the individual sections (A). Optionally an overall test result (GA) of the preliminary film product (FVP) is also ascertained in dependence of the rating result data (B). Furthermore a method for correcting a preliminary film product (FVP) is described. In addition a preliminary film product testing device (20) is described. Moreover a preliminary film product correcting device is described.

15 Claims, 14 Drawing Sheets

Figure 1:
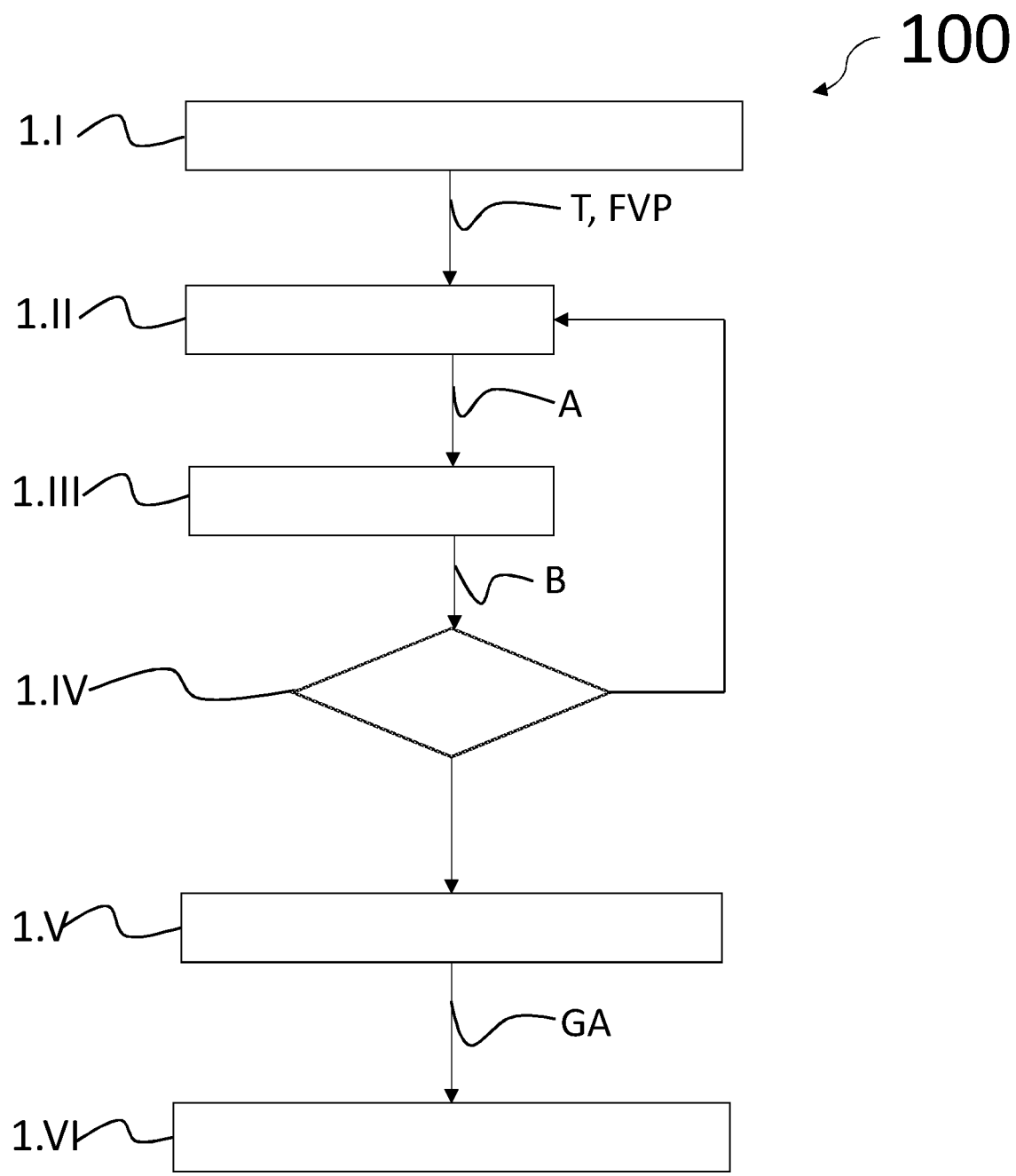

(51) Int. Cl.
  *H04H 60/31*     (2008.01)
  *H04N 21/466*    (2011.01)

(56) References Cited

U.S. PATENT DOCUMENTS

| | | | |
|---|---|---|---|
| 7,212,988 B1 * | 5/2007 | Feldten | G06Q 30/02 |
| | | | 725/24 |
| 8,086,577 B2 * | 12/2011 | Handy-Bosma | H04N 21/4756 |
| | | | 707/694 |
| 10,645,460 B2 * | 5/2020 | Paul | G06Q 50/01 |
| 10,897,647 B1 * | 1/2021 | Hunter Crawley | |
| | | | H04N 21/8547 |
| 2003/0226145 A1 * | 12/2003 | Marsh | H04N 7/163 |
| | | | 725/47 |
| 2008/0222671 A1 | 9/2008 | Lee et al. | |
| 2010/0211439 A1 * | 8/2010 | Marci | H04N 21/4662 |
| | | | 705/7.29 |
| 2013/0280682 A1 * | 10/2013 | Levine | A61B 5/486 |
| | | | 434/236 |
| 2014/0359648 A1 * | 12/2014 | Yin | H04N 21/44226 |
| | | | 725/14 |
| 2015/0143392 A1 | 5/2015 | Silveira-Filho et al. | |
| 2017/0134803 A1 * | 5/2017 | Shaw | H04N 21/234363 |
| 2017/0169726 A1 * | 6/2017 | Aguirre | G09B 5/02 |
| 2017/0308931 A1 | 10/2017 | Jaeger | |
| 2018/0241864 A1 | 8/2018 | Males et al. | |
| 2018/0260724 A1 | 9/2018 | Blanco et al. | |
| 2019/0171666 A1 * | 6/2019 | McKenzie | G06F 16/5866 |
| 2019/0297384 A1 * | 9/2019 | Bist | H04N 21/25891 |
| 2019/0379938 A1 * | 12/2019 | Salo | G06N 20/20 |
| 2020/0029884 A1 | 1/2020 | Arai et al. | |
| 2020/0296480 A1 * | 9/2020 | Chappell, III | H04H 60/33 |
| 2021/0195300 A1 * | 6/2021 | Thattamangalam-narayanan | |
| | | | H04N 21/44222 |
| 2022/0030080 A1 * | 1/2022 | Parra | A63F 13/60 |
| 2023/0245143 A1 * | 8/2023 | Nogueira, Jr. | G06Q 30/0217 |
| 2023/0315825 A1 * | 10/2023 | Dufour | G06V 10/761 |
| | | | 713/186 |

* cited by examiner

TESTING OF A PRELIMINARY FILM PRODUCT

The invention relates to a method for testing a preliminary film product. The invention also relates to a method for correcting a preliminary film product. Further subjects of the invention are also a device for testing a preliminary film product and a device for correcting a preliminary film product.

In the production of films it is difficult to assess in advance, whether a film material later becomes a film accepted by a target audience later becomes a film or not. During its production a film passes through various stages of development. For example, a synopsis is prepared first in terms of the development process, which delivers a first overview about the film's subject matter. Later on, a so-called treatment is developed, which can be regarded as a preliminary form of a script. A treatment shall convey the complete dramaturgically coherent narrative of a film, but without containing formulated scenes with complete dialogues, as is the case with a complete script. Finally the actual script is generated. Thereafter film footage is created of individual scenes of the film.

All these preliminary and intermediate steps are not only very time-consuming but also require electrical energy and other resources, such as sets, props, which in part have to be especially made and may be destroyed again in a scene, or expenditure for the travel of whole teams, which if only from an environmental point of view, should be avoided as far as possible.

It would be desirable to be able during the individual stages of film development to make predictions as regards the later success with the target audience in order to save on resources during film production.

Up to now it has been possible to rate a film material by engaging a few individual experts. Furthermore there exist approaches to arrange for an evaluation to be made with the aid of big data, which is used for instructing and training a neuronal network (artificial intelligence). In addition crowd-based processes are used to assess the prospects of success of a film. There is also the possibility of generating a pre-visualisation of a prototype of a film, by means of which an assessment is made of the later acceptance by the target audience. If a lot of experts are engaged for assessing the prospects of success, this process in itself may require a great deal of time and other means and may not make it possible to give an adequate risk-and-chances assessment because the view of the target group is not taken sufficiently into consideration. An additional difficulty here is the fact of not being able to uniformly evaluate feedback.

It is therefore an objective of the present invention to propose an improved method of assessment and analysis and a technical device suitable for this, which in the various stages of a film production can be employed for predicting the likelihood of success and for improving the existing preliminary film product/the final film.

This objective is achieved by a method for testing a preliminary film product according to claim 1, a method for correcting a preliminary film product according to patent claim 11, a preliminary film product testing device according to claim 14 as well as a preliminary film product correcting device according to claim 15.

With the inventive method for testing a preliminary film product the preliminary film product is initially submitted, i.e. made available/presented to a selected group of test persons. The presentation may comprise a visual display, a text display, a film or an acoustic reproduction as well as random combinations of the types of presentation named. The presentation is preferably made with the aid of a technical system such as a PC, a laptop, a notebook, a tablet or a smartphone. The preliminary film product is a preliminary result generated during the process of producing the film, which, prior to completing the film production/before the end product of the film production is generated, already permits an overview of the course of action as well as of further partial aspects of the end product.

The preliminary film product represents previously generated information, for example a summary of the respective film product. The film product as such is then generated in the process of the film production chronologically after the preliminary film product. The film product itself is the end product of the film production, as a rule the completed film.

This involves dividing the preliminary film product into individual sections for a finer resolved assessment/examination. If for example the preliminary film product comprises a rough textual summary of the action of a film product, which is read by or read to the test person, the text may for example be divided into individual chapters or scenes, paragraphs and sentences/semi-sentences etc. If the preliminary film product is a film, the film for example may be broken down into individual scenes/moments, as sections.

The actual testing and assessment operation begins with the receipt of the individual sections of the preliminary film product by the test persons, and at the same time or immediately thereafter the test persons generate a plurality of different reaction signals, which preferably comprise information as regards their conscious or subconscious reactions to the received sections of the preliminary film product.

These section-related reaction signals, be they generated consciously or subconsciously, are then recorded with the aid of sensors for example. For example, the recording may be effected by an input operation of the test person, in which a physical signal is recorded created by a conscious input action of the test person via a user interface. However the recording may also be realised by a sensor-based measurement of a preferably subconscious physiological reaction of the test person. This issue will be explained in more detail at a later stage.

At this point it is pointed out that "dividing" (breaking down) the preliminary film product into individual sections of the preliminary film product may preferably be carried out prior to a presentation of the preliminary film product, i.e. the work is as mentioned above preferably divided into predetermined "content-related" sections, which depend on the content of the work such as chapters, scenes etc. This breaking down may occur as early as directly during preparation of the preliminary film product/may already have been defined by a product of a previous production stage. Basically however, the sections may also be simply determined chronologically and/or quantitatively (or time-duration-related and/or quantity-related), e.g. each section encompasses a certain time duration, which is required (at least estimated) during the presentation/receipt, or a certain volume (for example a certain amount of text, in particular a line). Different breakdown methods may also be used in combination, e.g. a breakdown into content-related sections and a further time-duration-related and/or quantity-related breakdown or a parallel use of both methods. The most advantageous variant may depend on the type of preliminary film product and the type of presentation. In the following, it is assumed as a preferred example, without restriction of generality, that initially (at least also) a breakdown of content-related sections is performed insofar as this is not mentioned otherwise. The section/the limits thereof may also be marked in a suitable manner.

The complete preliminary film product can be presented to the test persons section by section respectively, possibly with pauses in between, in order to record the reaction signals. The entire preliminary film product can be presented depending on the type of product, but also contiguously, and the respectively recorded reaction signals are assigned to the section respectively recorded (at the same time) in connection therewith. A "breakdown" into sections, by the way, can also be performed e.g. automatically, during the presentation of the preliminary film product/the receipt by the test persons, in particular if the breakdown is a chronological or quantitative breakdown. A further refined breakdown of the section into partial sections is also possible with the method.

Next, as part of the testing operation, an automatic evaluation of the recorded reaction signals is performed in order to, in this way, generate rating result data of the individual sections which is based on the reaction signals recorded for the respective section, i.e. subconscious reactions and/or assessments of the test persons. As part of this evaluation rating result data is then generated, which includes information as regards the subjective quality of individual sections of the preliminary film product and thus also the film product to be generated at a later stage.

Advantageously a prediction can already be made at an early stage as to the likelihood of success of a film material thus reducing an unnecessary use of resources during a production. Evaluation may for example be realised on the basis of a model relationship between possible reactions of the test persons and the individual influence variables, which are connected with the later success of a film product. The evaluation can however also be implemented with the aid of AI based techniques. For example a neuronal network may be generated/trained on the basis of training data with the aid of a so-called deep-learning algorithm, which ascertains the desired result data by way of the recorded reaction signals. A concrete example for this will be discussed at a later stage. This particular variant can be particularly flexibly adapted to the characteristics of different test groups and test requirements. Evaluation may also be performed partially with the involvement of experts.

For example, one or more experts may evaluate the texts/verbal reactions of the test persons, whilst non-verbal reactions are evaluated in an automated manner.

Optionally an overall test result of the preliminary film product may also be ascertained in dependence of the rating result data, in order to offer a simplified decision aid to the persons involved in the film production. Advantageously the overall result provides information on the likelihood of success and the quality of individual passages as well as the entire film. The overall result is composed of a combination of ratings from a plurality of test persons and, for a sufficiently large number of test persons, permits an approximate objective assessment (generated by subjective individual estimates) of the likelihood of success of a film passing through the production process. Advantageously both the rating process and the evaluation process are largely or even completely performed in an automated manner with the aid of technical means, so that an involvement of experts for preparing an expert opinion as regards the likelihood of success can be avoided thus saving the costs incurred thereby.

With the inventive method for correcting a preliminary film product, initially the inventive method for testing a preliminary film product is performed and thereafter the next version of the preliminary film product is generated in dependence of the rating result data of the performed method. In other words, a correction of the current concept of the film product/a modification of the preliminary film product is performed, so that the product/preliminary product generated in the current stage is improved/modified in such a way that the later film product has an improved likelihood of success with the desired target audience. Advantageously the manufacturing process of a film may encompass one or more correction phases, in which a largely or completely automated correction of intermediate stages or end stages of a film production takes place. The correction is performed on a broad data basis and in this way obtains a higher degree of objectivity in comparison to a correction on the basis of the opinion of individual experts, which contributes to enhancing the likelihood of success of the manufactured film product.

In particular, this also involves repeatedly checking and correcting a preliminary film product in an iterative process, wherein the test person group can also be adapted between the iterative steps.

The preliminary film product testing device according to the invention includes a playback unit for providing a preliminary film product to a selected circle of test persons. A part of the preliminary film product testing device may also be a structuring unit for dividing the preliminary film product into individual sections in order to obtain a finer resolution of the assessment/examination, for example in order to divide the preliminary film product into predetermined, in particular content-related sections.

If the preliminary film product for example includes a rough textual summary of the action of a film product, the text is then divided into individual chapters/scenes, paragraphs and sentences/semi-sentences. If the preliminary film product is a film, the film is divided into individual scenes/moments, as sections.

However, as already mentioned the preliminary film product may have already been divided into suitable sections during its creation and provided e.g. with corresponding section markings.

The preliminary film product testing device according to the invention additionally includes a recording unit for the section-wise recording of reaction signals of test persons during or simultaneously with or immediately after receipt of the preliminary film product by the test persons. The section-wise recording is understood to mean in particular that the individual reaction signals are unequivocally assigned to a certain section so that a finely resolved examination and assessment of the preliminary film product is possible. If in particular breakdown should not take place until e.g. during the presentation, the breakdown/division into sections could also be performed by the recording unit and/or the playback unit/any other unit, in particular if a time-duration-related and/or quantity-related breakdown is intended.

Assignment of the reaction signals to a certain section can be ensured by means of a suitable communication/synchronisation of these different units/the structuring unit and/or by utilising section markings.

The reaction signals are based on the reactions and/or assessments of the test persons and are present as physically measurable signals.

A part of the preliminary film product testing device is also a rating data ascertaining unit, which is arranged to perform an automatic evaluation of the recorded reaction signals in order to generate rating result data of the individual sections on the basis of the recorded reactions and/or assessments of the test persons. The rating data ascertaining unit, also called rating unit, may comprise further units, for example a test analysis unit, with which the text inputs are analysed for their significance whereby a quantitative variable is generated based on the significance. The preliminary film product testing device may also optionally include a result ascertaining unit for ascertaining an overall test result of the preliminary film product in dependence of the rating result data. The preliminary film product testing device according to the invention shares the advantages of the method according to the invention for testing a preliminary film product.

The preliminary film product correction device comprises the preliminary film product testing device as well as a correction unit for modifying the preliminary film product in dependence of the rating results of the preliminary film product testing device according to the invention. The correction unit, in a simple realisation, may be arranged to eliminate a section rated as being not very promising in the preliminary film product. In a more complex design the correction unit may for example accept inputs of a person involved in the film production for modifying a section or partial section of the preliminary film product. The preliminary film product correction device according to the invention shares the advantages of the inventive method for correcting a preliminary film product.

Parts of the inventive preliminary film product testing device and the preliminary film product correction device may for the most part be constructed in form of software components.

In particular this applies to parts of the playback unit, the structuring unit, the recording unit, the rating data ascertaining unit and the result ascertaining unit as well as the correction unit. However, the components may also be partially realised in principle, in particular when quick calculations are called for, in form of software-supported hardware, for example FPGAs, PLD or the like. Equally the required interfaces, for example if merely a take-over of data from other software components is at stake, may be designed as software interfaces. They may, however, also be designed as interfaces constructed from hardware, which are controlled by suitable software.

A realisation partially consisting of software has the advantage that it is possible to retrofit computer systems already used in the film production and networks in a simple manner by means of a software update in order to operate in the inventive manner. Insofar the objective is also met by a corresponding computer program, which can be directly loaded into a storage device of such a computer system, with program sections, in order to execute all steps of the method for testing a preliminary film product or the method for correcting a preliminary film product, when the computer program is executed on the computer system.

Such a computer program product may include, apart from the computer program, additional constituents as required such as documentation and/or additional components, also hardware components such as hardware keys (dongles etc.) for using the software.

Transport of the storage device of the computer system and/or storage in the computer system may be effected using a computer-readable medium, such as a memory stick, a hard disc or another transportable or firmly installed data carrier, on which the program sections of the computer program are stored, the program sections being readable and executable by a computer unit. To this effect the computer unit may comprise for example one or more cooperating microprocessors or the like. In addition the transmission of the computer program and the storage of data may be effected also via the internet/a cloud-based solution.

Preferably such a computer program product may be designed as a modular software solution, which can be extended by hardware components. In such a design the software includes a server program, which is stored on a computer of e.g. a film production company or on cloud. Furthermore the software also includes an app, which is stored, respectively, on the so-called client devices, preferably terminal devices such as smartphones, of the test persons. If then a preliminary film product is to be tested with the method according to the invention, the preliminary film product is transmitted with the aid of the server program to the clients, for example the smartphones of the test persons. The test persons can now, with the aid of the app, view the preliminary film product or listen to it and generate reactions with corresponding state signals and assessments with corresponding input signals. The app comprises program parts, with which sensors of the client/smartphone are controlled for recording the reactions and assessments. The app may for example provide a scroll tracking capability. Moreover a camera is used by the app for recording eye movements or skin colour of the test person. The camera to be used for recording the physiology of a test person may for example be a camera integrated in for example a smartphone of the test person. Furthermore the app may include capabilities for measuring the reading speed, for example based on the eye movements or on the scrolling speed/the scrolling behaviour. In addition the app may comprise a capability for assigning measuring times and/or input times to the recorded reactions and assessments. In other words, each time a signal connected to a reaction is recorded or each time an input is recorded, which is recorded as part of a transmission of an assessment information from the test person to the app, the point in time of the measurement/input is recorded, and measuring events recorded at the same time or at a time very close to it are assigned to a certain sub-section or subject matter of a section. Using the app, it is also possible to integrate devices incidentally present with the test person and equipped with sensors for measuring biometric data, in the testing operation.

For example a sports watch or smartwatch may be integrated with the aid of the app in the testing operation and used for measuring a pulse frequency or skin temperature.

Preferably the app converts the recorded signals into measured values or input texts. The server program receives the measured values and input texts determined by the app as part of the assessments and reactions of the test persons and conducts an evaluation on the basis of the transmitted information in order to generate rating result data for the individual sections of the preliminary overview. In the evaluation the reactions and assessments generated by the individual test persons are combined to form a rating result of the individual sections. The server program also conducts further processing steps, such as ascertainment of an overall test result as well as a correction of the preliminary film product in order to improve the chances of success of the film production.

Further particularly advantageous designs and further developments of the invention are described in the dependent claims as well as in the description hereunder, wherein the patent claims of a certain category can also be further developed according to the dependent claims of another category, and features of different exemplary embodiments can be combined to form new embodiments.

The reaction signals recorded as part of the method for testing a preliminary film product may include input signals or state sensor signals. An input signal is understood to be a signal, which is consciously transmitted by a test person via an interface. The input signal includes information, which is consciously generated and transmitted by the test person. State sensor signals on the other hand are generated by sensors, which measure the state, in particular a physiological or biometric state of a test person. The state sensor signals thus include information, which can be evaluated in order to ascertain information on the emotions and the subconscious attitude of the test person in relation to the preliminary film product.

Reactions and/or assessments may for example be generated by a conscious input of a test person via a user interface. For example a test person actuates an input button or directly or indirectly touches a rating field with a pointing device on an image display device provided for such an input. Such a device may for example be a touchscreen, a touchpad or similar. Conscious inputs have the advantage that they are much differentiated and can be utilised directly thus allowing information generated therewith to be easily evaluated.

A state sensor signal is suitable in particular for the recording of biometric or physiological data, which are generated for example subconsciously by a test person. Subconscious reactions may make themselves felt through physiological phenomena or other instinctive movements or changes in physical conditions such as a change in body temperature, skin colour, sweat production, blood pressure or heart frequency. Such phenomena may be recorded by a sensor-based measuring of biometric and/or physiological data of the test persons. The measuring of subconscious reactions has the advantage that these can hardly be influenced deliberately by the test person and are thus authentic and cannot be easily manipulated. Moreover when recording subconscious reactions/reaction signals based thereon, the test person need not cooperate, which is of advantage in particular with children as test persons. Moreover, when selecting film consumption, emotional aspects are above all the deciding factor, which given instinctive reactions, can be recorded even more authentically and more accurately than is possible with the aid of detailed and thought-out conscious assessments.

Given the case that several different reaction signals are recorded within a very short time, these reaction signals can be assigned to a sub-section of a section. Such a sub-section may for example encompass several sentences or exactly one sentence or semi-sentence of a text or dialogue or, in case of a film, a scene/a dialogue sequence, or a certain time duration, e.g. a second. Sub-sections (like the sections themselves) may basically be chosen in a content-related, time-duration-related and/or quantity-related manner.

In this way different reactions and/or assessments can be associated with a common sub-section of a section. This association may for example be realised by means of ascertaining and assigning a measuring time or input time to the respective different reaction signals. Now if different reaction signals comprise the same measuring or input time or are ascertained within an at least chronologically very close time span, they can be assigned to one and the same subject of the assessment or reaction. In this way a rating of a sub-section can be made based on a broader basis of measured data.

If different reaction signals preferably based on subconscious or conscious reactions and/or assessments are recorded, then—in case they are, as previously described, to be assigned to one and the same sub-section and are thus indirectly related to each other—a consistency test may be performed by way of these different sources of information.

Preferably at least one subconsciously generated reaction signal is taken into account during the consistency test. This consistency test is carried out in particular between consciously and subconsciously generated ratings data. Such a consistency test makes it possible to check the quality and closeness to reality of reactions and/or assessments. For example it may happen that a test person would albeit like to cash in on the remuneration scheduled for the test, but does not feel like going through the test procedure as such and therefore performs the test carelessly and without any interest. The test result generated by this person may, due to the disinterest of this person, be possibly worthless or may even have a negative effect on the reliability of the overall result, if the test person inputs arbitrary ratings or deliberately false ratings. If due to the subconscious behaviour reaction signals are then recorded which include physiological or biometric data and if these data recorded at the same time/relating to the same production sections contradict conscious reactions, it can be concluded that the test person was not engaged and that it would be better to ignore their test result. It could also be that during the test the test person was distracted, so that the test person, possibly only from time to time, for example during receipt of a single section or just a few sections of the preliminary overview, does not deliver a usable reaction or assessment. Again, such a transient lapse/disruptive effect can be detected with the aid of a consistency test. In such a case the assessment of the respective sections can then be neglected in an overall rating, whilst sections which were received without distraction by the test person/their assessment are included in the end result. In this way even a partial usability of a test procedure can be accurately detected and taken into account during evaluation.

In a particularly practicable design of the method according to the invention for testing a preliminary film product, the preliminary film product comprises at least one of the types of playback:
 a text,
 an audio version of the film material,
 a film presentation.

A playback of the text allows a test person, reading at their own speed, to record even details of the preliminary overview and to quickly supply both an intuitive and a detailed and well-thought-out, purely subjective rating. Besides this type of playback is suitable, above all, for an early phase of the film production, where normally a preliminary film product is only available in form of a written summary such as a synopsis, a treatment or a script.

An audio version of the film material, for example in form of an audio book or a text-to-speech playback, permits a particularly time-saving receipt of a film material, wherein the test person, at the same time, can also perform a parallel activity. For example the test person may, at the same time, perform a travel activity in a train, an endurance sports activity or a household activity such as cleaning or ironing or cooking, so that he or she does not need to sacrifice valuable time exclusively for the test procedure. Since with this variant a distraction of the test person is probable, at least at times, because of his/her main activity, the described consistency test can be utilised particularly advantageously in order to check, whether the test person happens to be distracted or is paying sufficient attention.

A film presentation, in particular during an advanced phase of the film production, permits a scenario comparable to the end product during playback/receipt by the test person, so that the reaction signals of the test person and the rating results based thereon are closer to reality and more reliable than for a playback of a text or audio version.

Such a film presentation may for example include dialogues stored on a graphic story board and noises or music. The film presentation may however also be realised through an animated film created via a game engine. Finally the film presentation may include a rough cut version of the film.

If generation of an input signal is to be effected by the test person as a reaction signal, the test person may be sent an input request signal, a so-called prompt signal, for rating a section of a preliminary film product. With a preferred variant a field with a gradual colour gradient or several colour bars may for example be displayed. The colour bars may for example be displayed on a screen at the end of each section and may be selected by the user, i.e. the test person, with the aid of a pointing unit such as a mouse.

Such a section may for example include a text, an audio clip, a graphics, in particular a moving graphics, or a film sequence or combinations thereof, which reproduce dialogues and/or an action. In the case of a text this normally comprises a plurality of lines up to about one to two pages of text, without there being any page switching between the pages. The text may be displayed as scrollable text as from a certain minimum length, so that the reader, without having to turn a page, can progress to the end of the text of the section.

As soon as the section has been read to the end/received, the reader/recipient changes to the next section by means of an input such as a click. However, with this advantageous design, instead of changing to the next section after a click by the reader, an input prompt is displayed with a button, which comprises a gradual colour gradient or several differently coloured buttons. The buttons may comprise, instead of different colours or additionally thereto, also other distinguishing features such as different textures, symbols or similar. With this advantageous variant the user can, by means of a single click, both change to the next section and at the same time supply a rating, in that he selects the coloured area at a point with a certain colour or, for a display of discrete differently coloured or textured buttons, selects one of these and in this way supplies a rating of the section he just read/received. With this arrangement a certain colour or texture is linked to a certain value of a rating. Not until the user/the test person has made his choice by means, for example, of a click, is the next section displayed to him, so that a rating of each individual section by the test person is ensured. In a particularly simple variant a button with only three colours, e.g. green, yellow and red, is displayed to the test person. Green means e.g. that the test person liked the section well, yellow means that the section could still be improved upon/was not wholly understood, and red means that the test person did not like the section. Such a firmly defined choice of a button or a colour allows the test person, once he has read/received a section, to supply a rating without any additional expense or time delay.

If a somewhat more differentiated rating of a section is desired, the button for the rating may be displayed with a continuous colour gradient, for example across the three named colours. The test person can then click on a random area and in this way supply a finely tuned rating. For example a section may then be given a random rating from 0% agreement to 100% agreement.

If the assessment is to be even more differentiated, a text field in response to a predetermined input signal such as a long click may be displayed to the test person, into which a free text comment can be entered. The two different types of rating can also be combined with each other. Also the input signal may be included in the rating as a reaction signal. In other words, the fact that the test person supplies a comment in the first place means that he/she finds the section particularly important. In addition also the content of the text may be evaluated for a rating.

If an even more precise rating for a section is required, individual sentences or semi-sentences of a section may be marked, in particular with a colour or a texture, in order to assess these.

It is also possible to display a field for an overall rating of the preliminary overview using a graphics display in the input prompt embodied by a prompt signal. With this type of rating the test person generates a graph, which depicts an agreement value in dependence of the current position in the text or the point in the film, for example in dependence of a section number and a line number, a point in time or a key scene. The agreement value may for example vary from 0% agreement to 100% agreement, so that a highly differentiated rating is possible.

If, in particular with an acoustic receipt of the preliminary overview, one wants to spare the test person as much effort as possible, an acoustic interface may also be realised for a rating issued by a speech input. Here an acoustic prompt signal may e.g. be initially generated. A rating issued by means of a speech input may consist of an oral indication of a scale value and/or of a free text comment. After suppling the rating, the next section is automatically read out/acoustically reproduced. Further the test person may send a stop command by means of a keyword for example, which is detected with the aid of voice recognition. The acoustic presentation is then stopped and the test person it given the opportunity to rate the sentence or semi-sentence just listened to. Thereafter the rating may also be supplemented by a free text comment, in order to give the producer or author additional valuable information for improving the section or passage. Supplying a scale value requires only a very small amount of time, whereas a free text comment reflects more specifically individual impressions and reactions of test person.

As already mentioned in part, a state sensor signal which comprises information as regards a subconscious rating, may consist of a reading speed measurement, a scroll tracking rating, a pulse value or an eye movement.

A pulse value provides information about the state of excitement of a person. A high pulse value may for example supply a clue that a test person finds a currently received section very exciting. A low pulse value is more likely to point to the fact that the test person is currently bored during receipt. Similarly an eye movement may also map an emotional participation of the test person.

When measuring the reading speed, a slow reading speed leads one to conclude that the section is boring, whereas a high reading speed indicates that the test person is fascinated by the received content. What is particularly relevant is the relationship between a currently measured reading speed and a normal reading speed of a test person. If a reading speed is considerably slower than the normal or average speed of the respective person, this also may point to a text, which is difficult to understand. An acceleration of the reading action by contrast leads one to conclude that the text passage is likely to be fascinating whilst a slow-down of the reading action makes one suspect that the text passage is boring. It cannot be excluded that the conclusions drawn from the behaviour of the test person could not also be contrary to the previous description.

In order to be able to link an individual reading behaviour with said implicit ratings such as interesting, boring or incomprehensible, a relationship can be worked out, with the aid of a training process for example, for every test person or a target group, between the reading behaviour of the test person or the target group to which the test person belongs and the interest of the test person/the target group. The relationships worked out during the training process by way for example of a larger number of test films or test scripts can be stored as labelled training data. The labelled training data can for example be used for generating a neuronal network or another system with artificial intelligence. The labelled training data, as input vector, comprises a plurality of measuring variables such as the reading speed and a deceleration or acceleration value of the reading behaviour. The labelled training data, as output vector, comprises parameter values for individual emotions or physical states such as values for boredom, interest, comprehension etc.

If the amount of time spent by the test person shall be kept short, input signals recorded during the test as such and state sensor signals can be evaluated and used in real time, so to speak, for ascertaining the searched-for relationship between the reading speed/the reading behaviour and an implicit rating of the test person preferably again with the aid of a neuronal network or another system with artificial intelligence (AI). With this version the training data is generated, so to speak, during the operation, so that the neuronal network/the AI system is constantly improved during the test process.

In the case of scroll tracking, if scrolling is slow, this may point to a slow reading speed and if it is fast this may point to an increased reading speed. Also scrolling upwards in order to re-read a paragraph or sub-paragraph may lead to the conclusion that there is interest in a text or a certain paragraph. It could also lead to the conclusion that a passage is difficult to comprehend. The said patterns can be correlated with rating variables using artificial intelligence. For example values of the measured variables of the subconscious behaviour of the test person can be correlated with a scale of assessment values. The assessment values may for example represent a measure for the interest, the agreement, the felt excitement or fascination or similar. In order to train a neuronal network, the behaviour patterns of the test person or target group in a training process may be determined and utilised for an input vector. Such an input vector as a parameter may comprise for example a scrolling speed and a scrolling direction. The output vector for a neuronal network may consist of parameter values to be determined for the extent of interest, the agreement, the felt excitement and the fascination. As part of the training process the test person explicitly indicates for example his/her emotions, so that the training data can serve as reference. After the neuronal network has been trained using the training data, it can then, on its own, determine the emotions of a test person, the target group or a very specific test person.

With one variant of the method according to the invention for the correction of a preliminary film product, in the step of creating the film product individual sections (assigned to the preliminary film product) are modified or sorted out, which according to a predefined rating standard were given an unfavourable rating. The rating standard may be laid down in advance also in view of the intended effects. For example a scene which creates too much fear may be rated as being bad in a children's film, whereas in a horror film for adults this effect would certainly be intentional.

Thus advantageously, on an objective basis without the expensive involvement of experts, the preliminary film product and thus also the later film product can be adapted in a simple manner without a great deal of expenditure, in order to improve the likelihood of success with the target group. Given the known affiliation of a person with a target group a target group of a film product may be more finely determined, from which then further optimisations may be derived.

Modifying a section may for example also comprise stipulating a suitable angle of view for the pictorial recording of a section. Apart from content-related modifications therefore modifications may also be made to the display/pictorial recording of a scene in order to improve the attractiveness of a film section for the target group.

With a particularly effective variant the different ratings of a test person based on input signals and state sensor signals are combined to give an overall rating of an entire text (or any other type of preliminary film product). The overall rating may for example comprise a diagram of one or more rating graphs in dependence of the time/the position in the text (or any other type of preliminary film product). The individual rating graph may for example be differently marked/coloured. But it is also possible, in the overall rating for a test person, to respectively generate a single rating graph ascertained by a weighted combination, e.g. addition of the variously created ratings. The overall rating can then comprise rating graphs of a plurality of test persons, which are depicted as "laid one above the other" in a common diagram. With this variant contradicting user opinions can be graphically depicted. Also the different graphs can be combined to form a single common graph. With this design improvement-worthy sections can be very easily recognised due to the uniqueness and simplicity of the display. Also test results of a potential test person can be compared to target-group-specific reference values, in order to ascertain whether a potential test person shall be selected for a future test or a future series of tests.

If the ratings of different test persons are to be weighted realistically, it is of advantage to know what the quality of the ratings of the individual test persons is, what the test persons' taste and affinity is with regard to individual genres of cinematic art. With the later criteria it is particularly relevant, to what extent the test person is different from the target group. If for example there is a big difference between the interest and the sense of style of the test person and the target group as regards a certain genre, the rating of the test person will be given a correspondingly weak weighting. The quality of the rating can for example be found out by an individual evaluation of a rating of a test person of a number of reference films, for example 100. The ratings of the reference films by the test person may for example be compared to the ratings by the target group or one or more qualified evaluating persons. The weighting of the rating of the test person then depends on the similarity of the ratings of the test person and the evaluating persons/the target group.

Weighting may also be performed by way of detailed text-based ratings of the reference films by the test persons. With this variant, experts such as producers assess the quality of the detailed ratings and are thus able to determine a weighting funded albeit in particular with corresponding additional expenditure.

The invention will now be discussed once more in detail with reference to the attached figures by way of exemplary embodiments. Identical components in the different figures are marked with identical reference symbols. As a rule the figures are not to scale.

Figure 2:
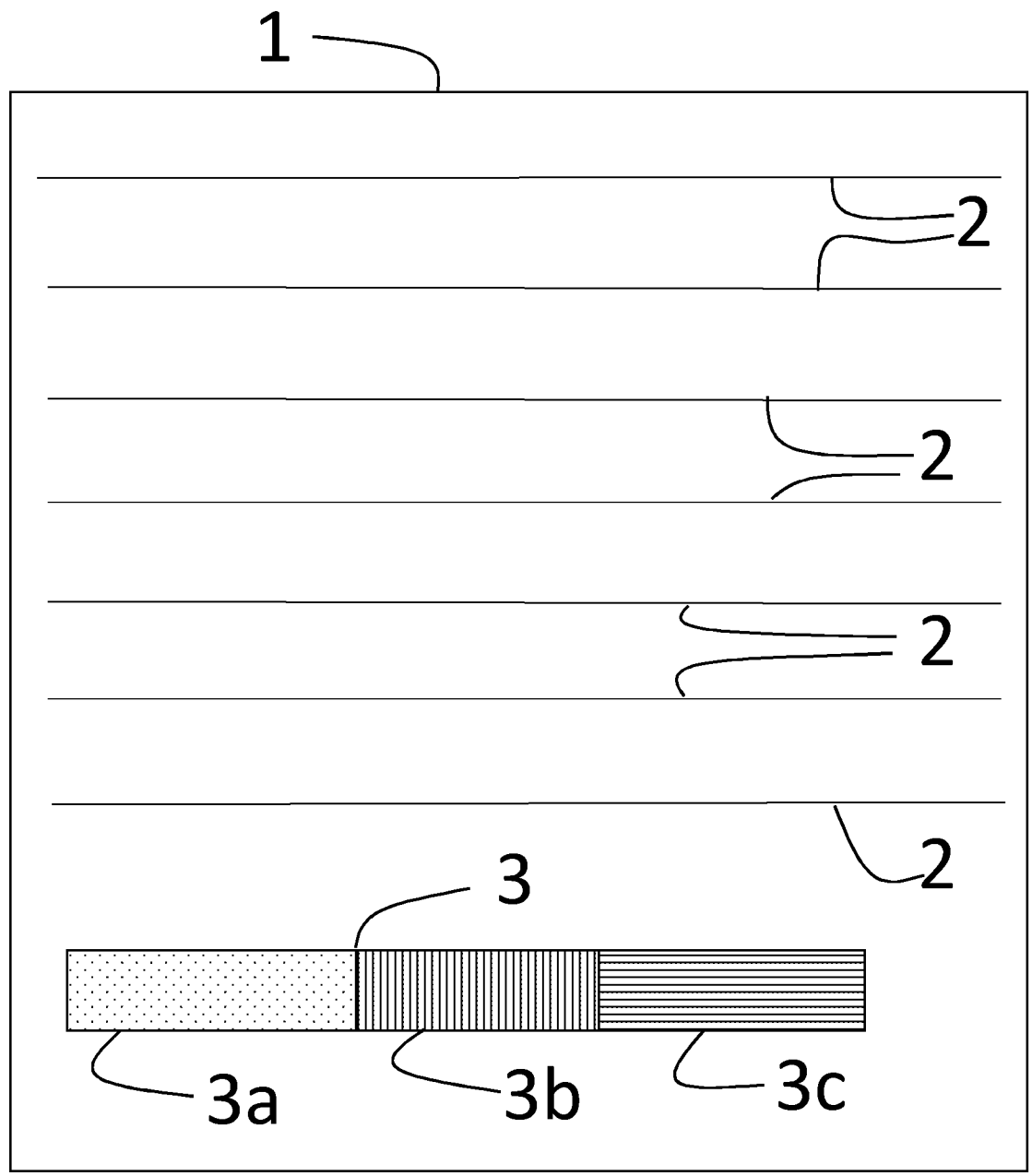
Figure 3:
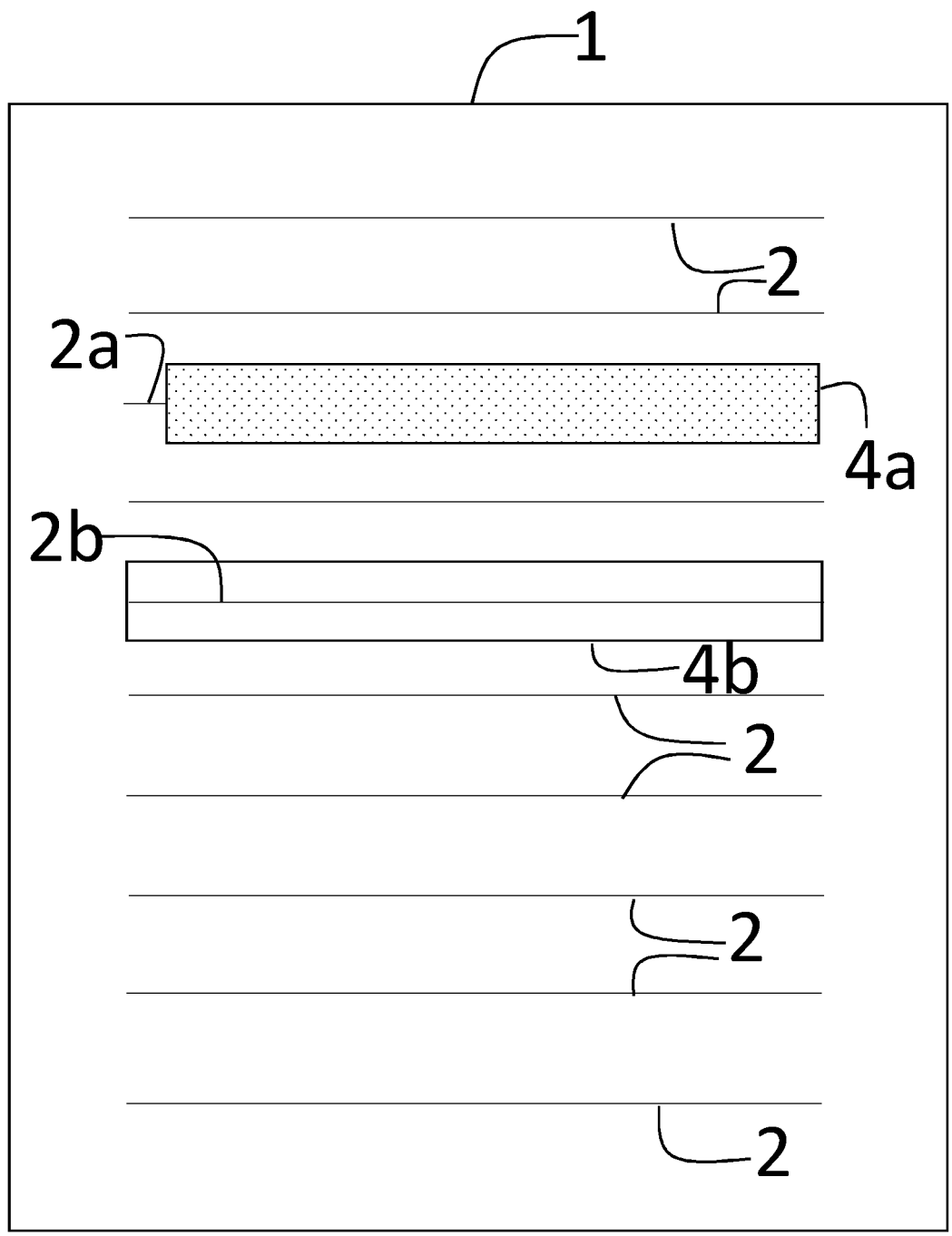
Figure 4:
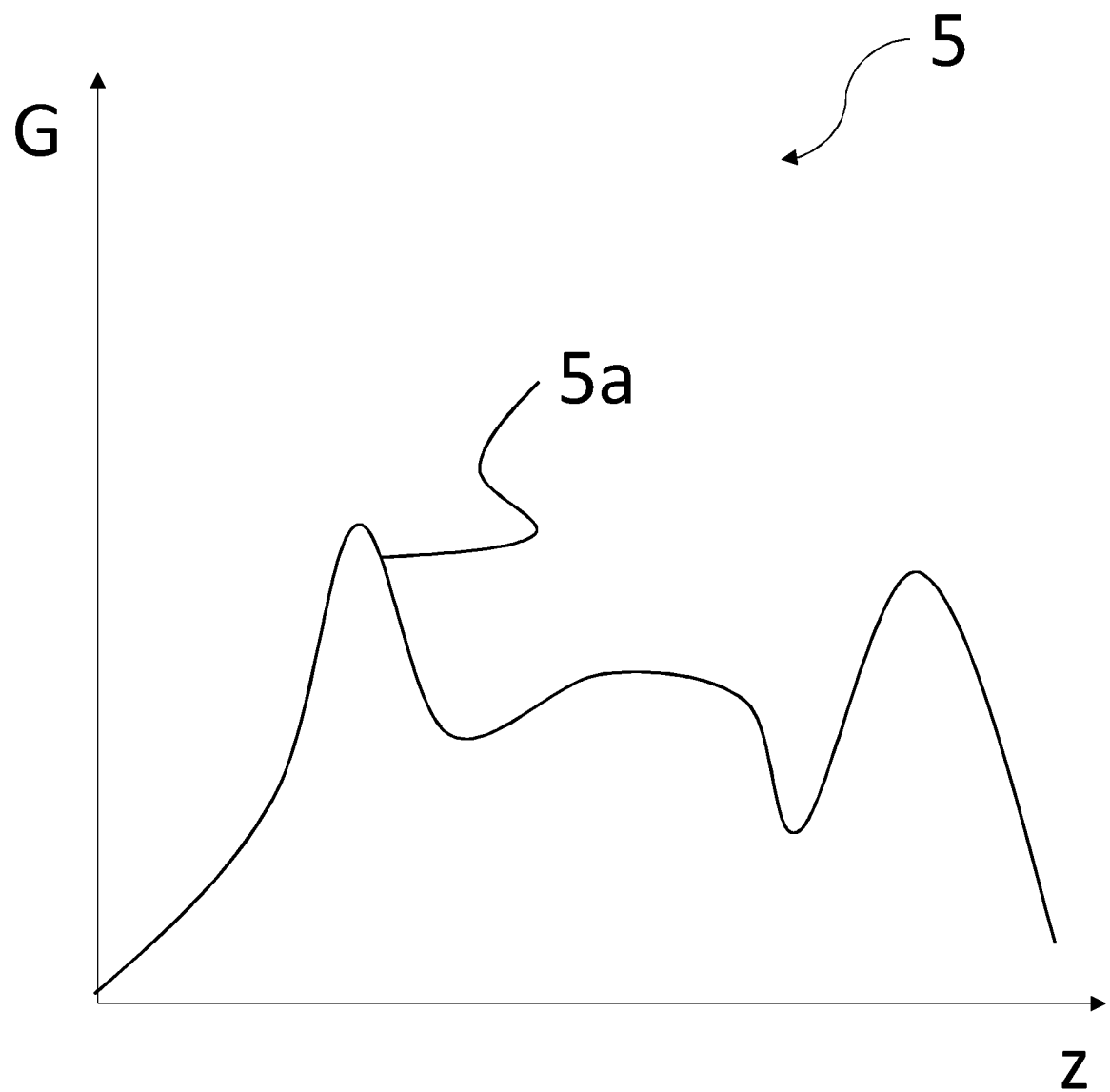
Figure 5:
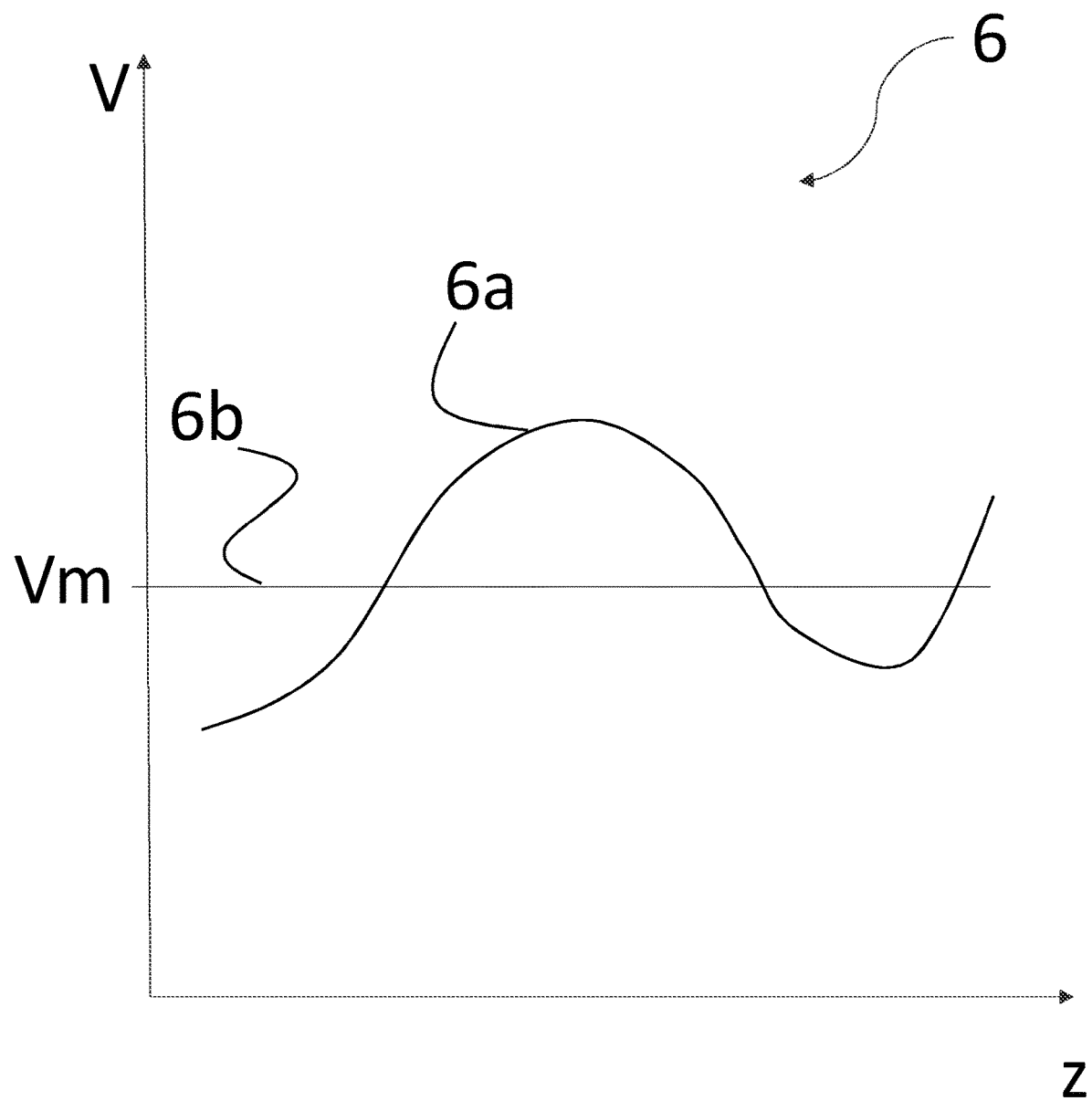
Figure 6:
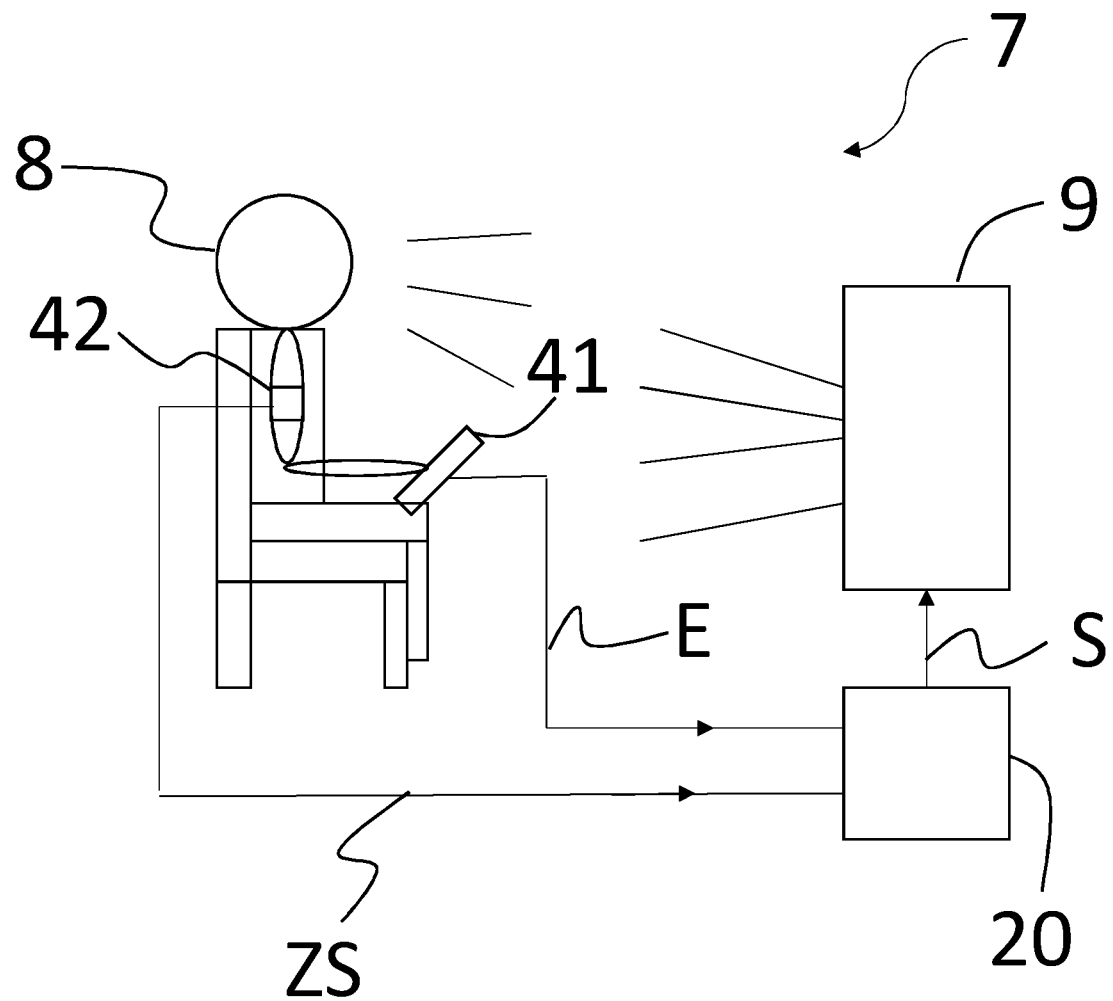
Figure 7:
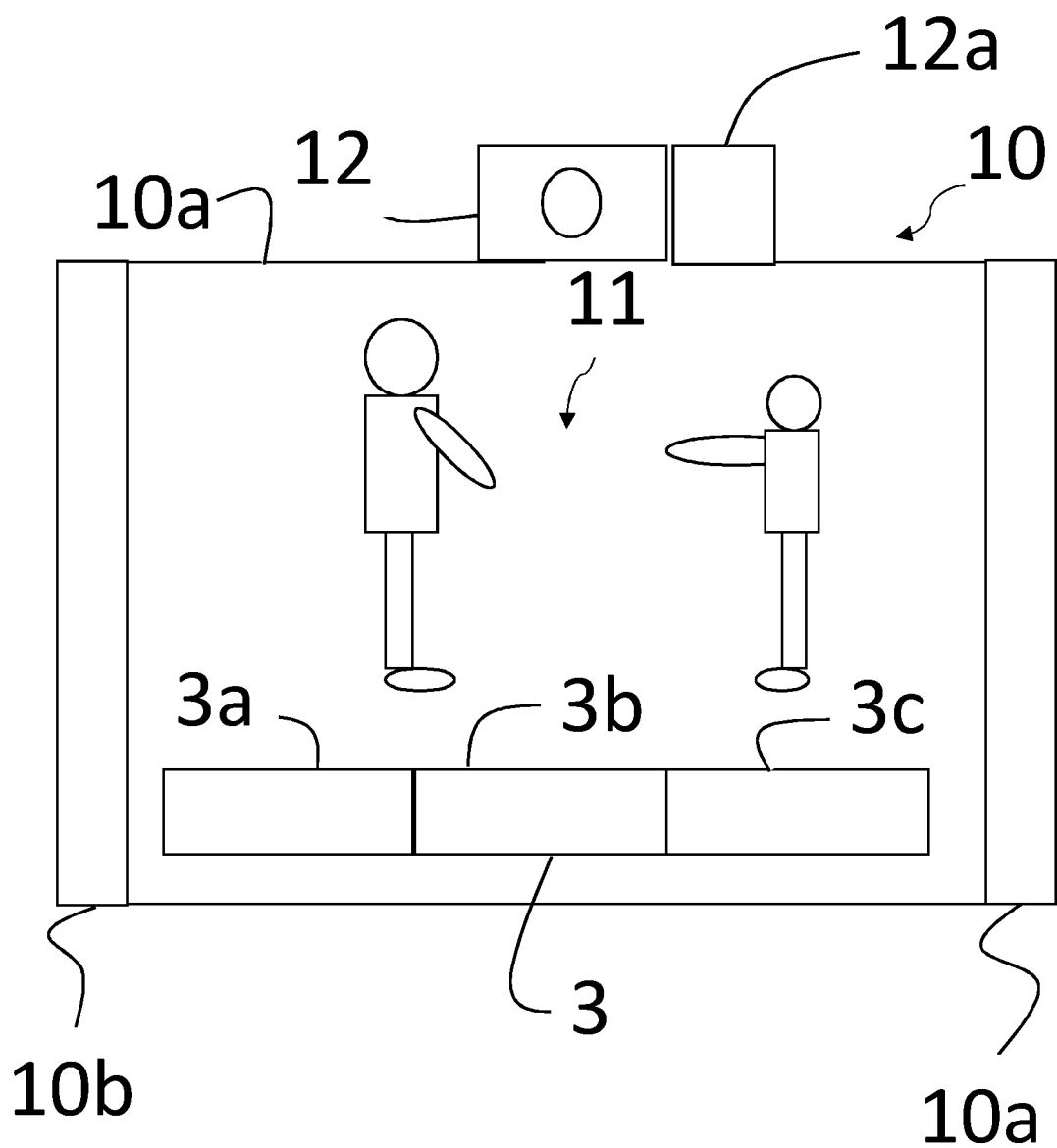
Figure 8:
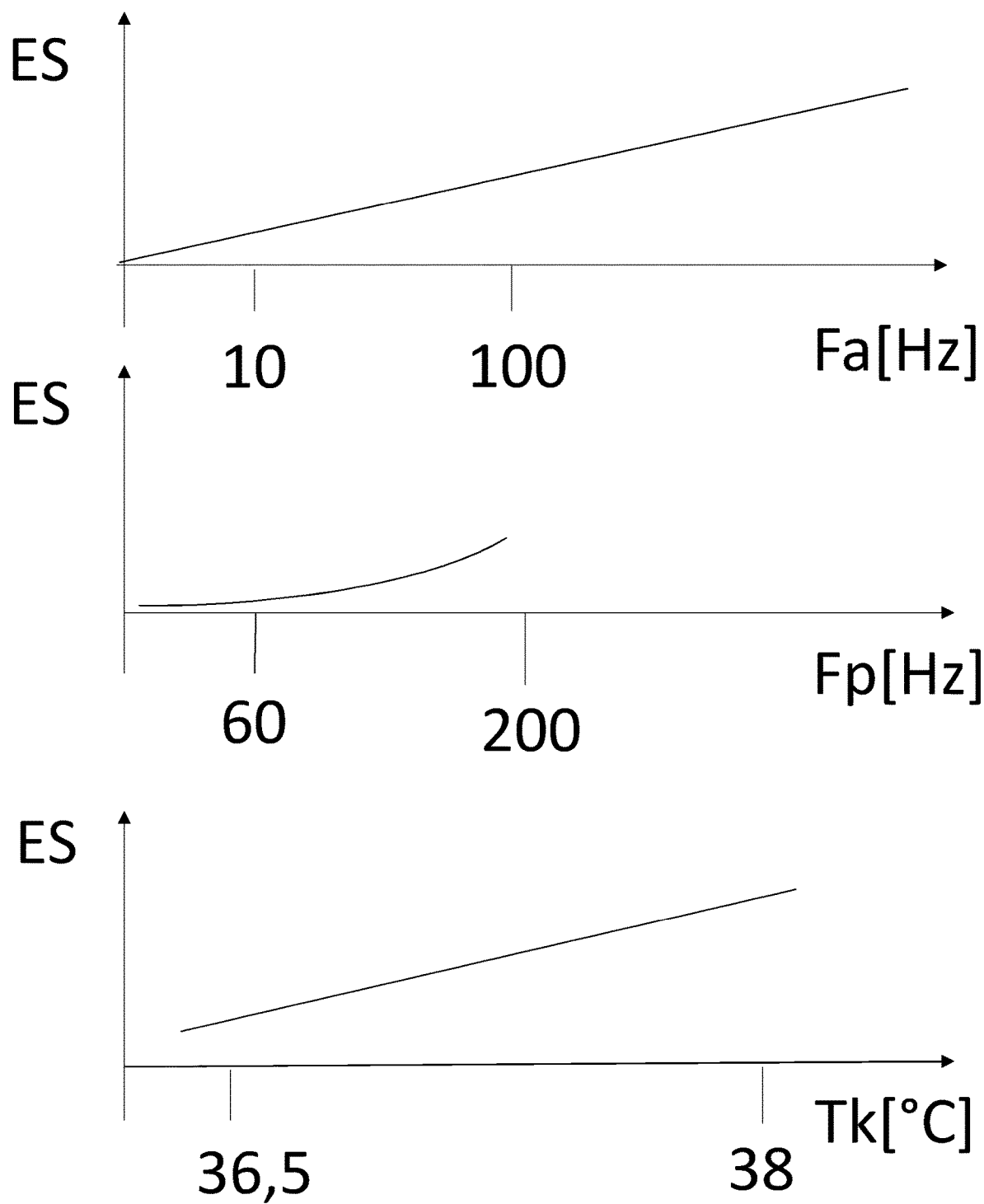
Figure 9:
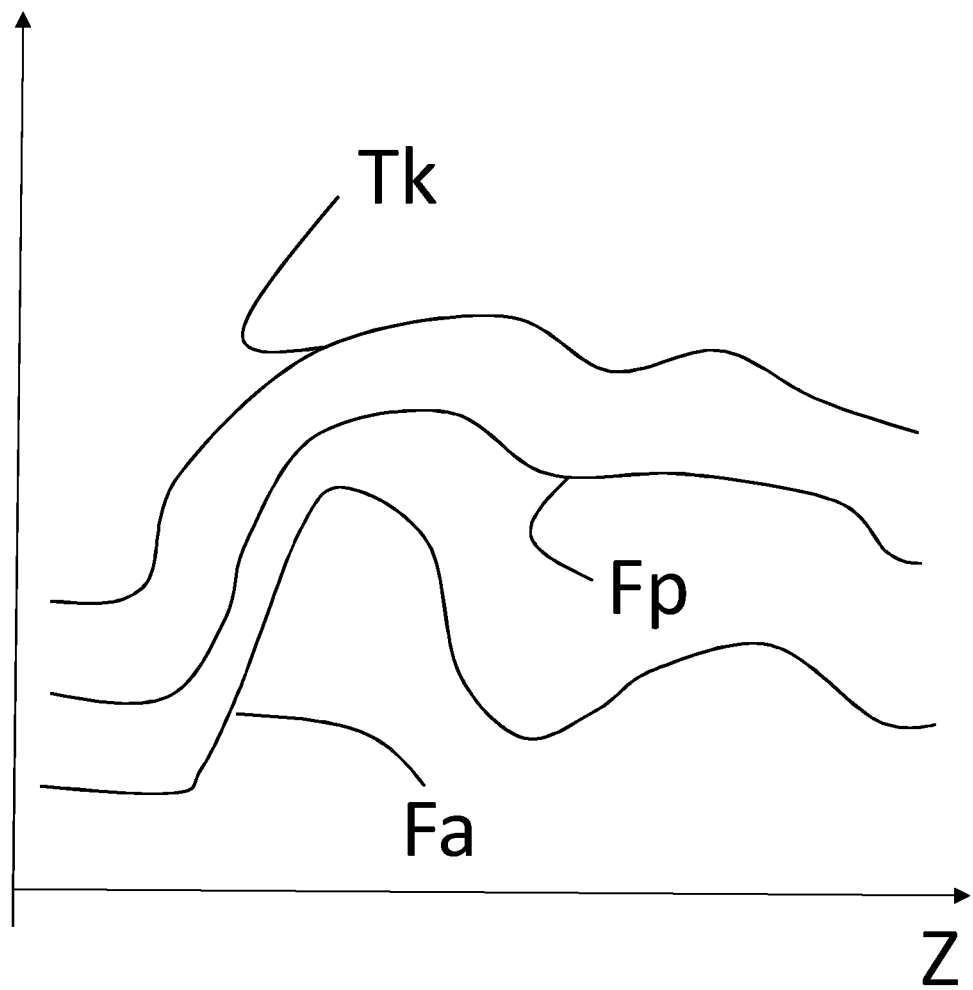
Figure 10:
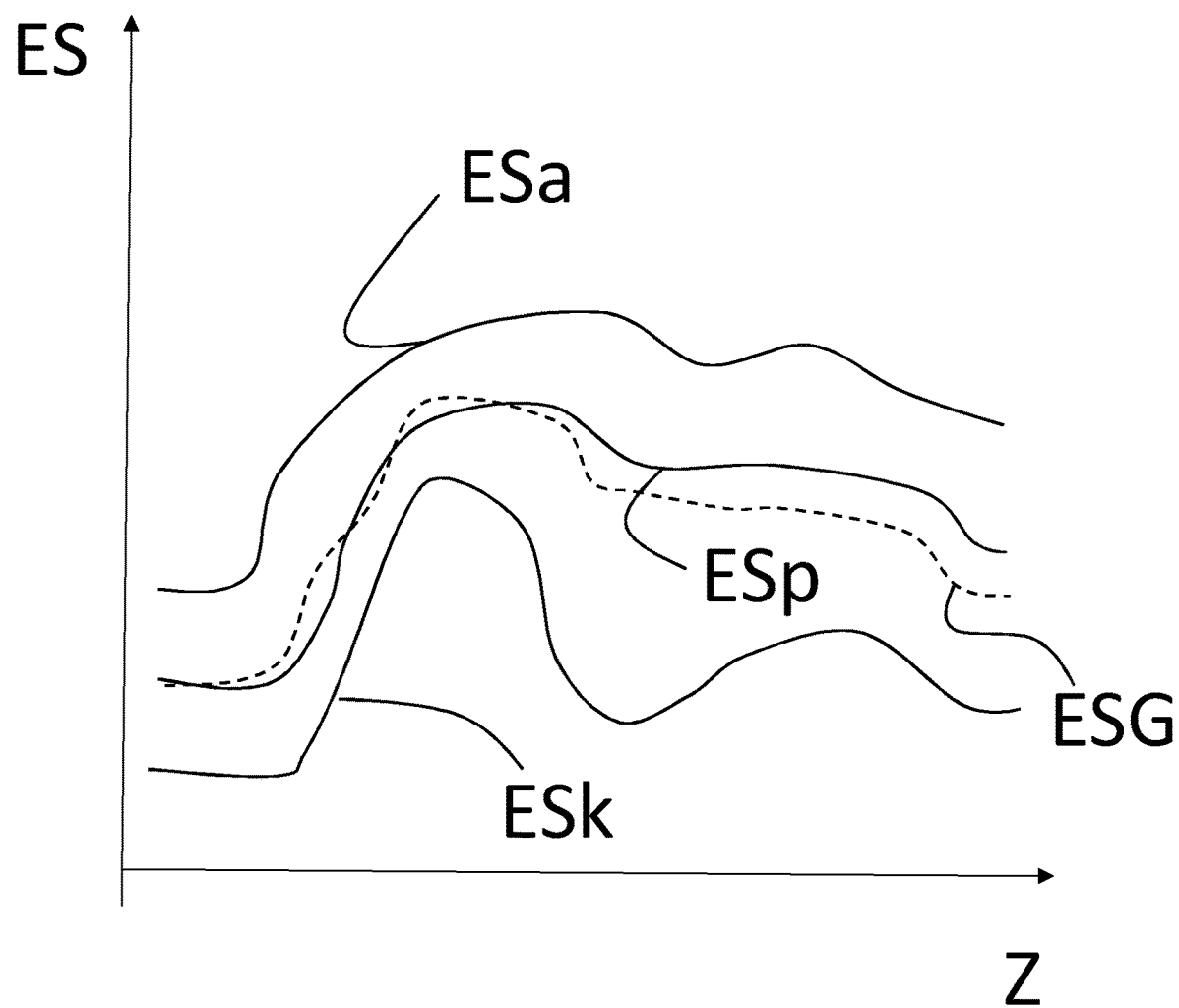
Figure 11:
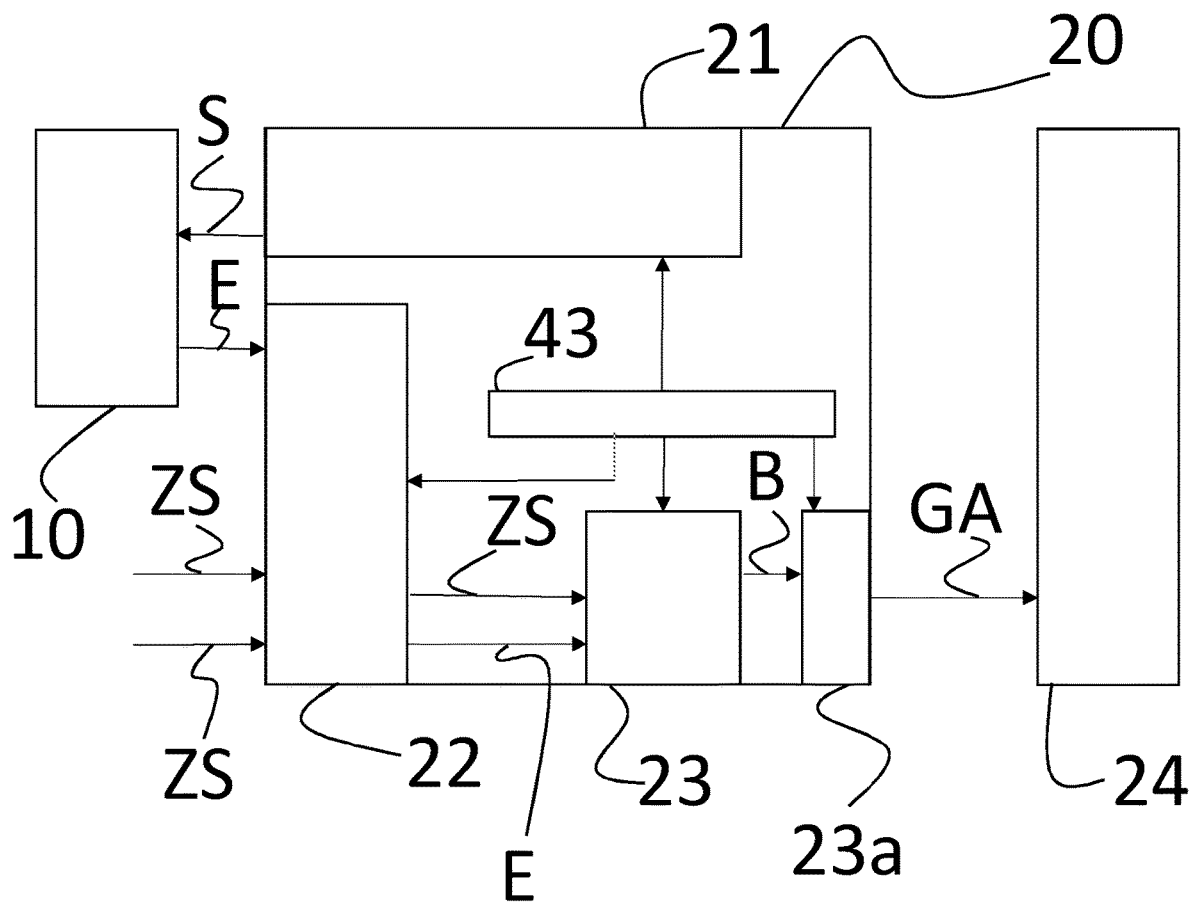
Figure 12:
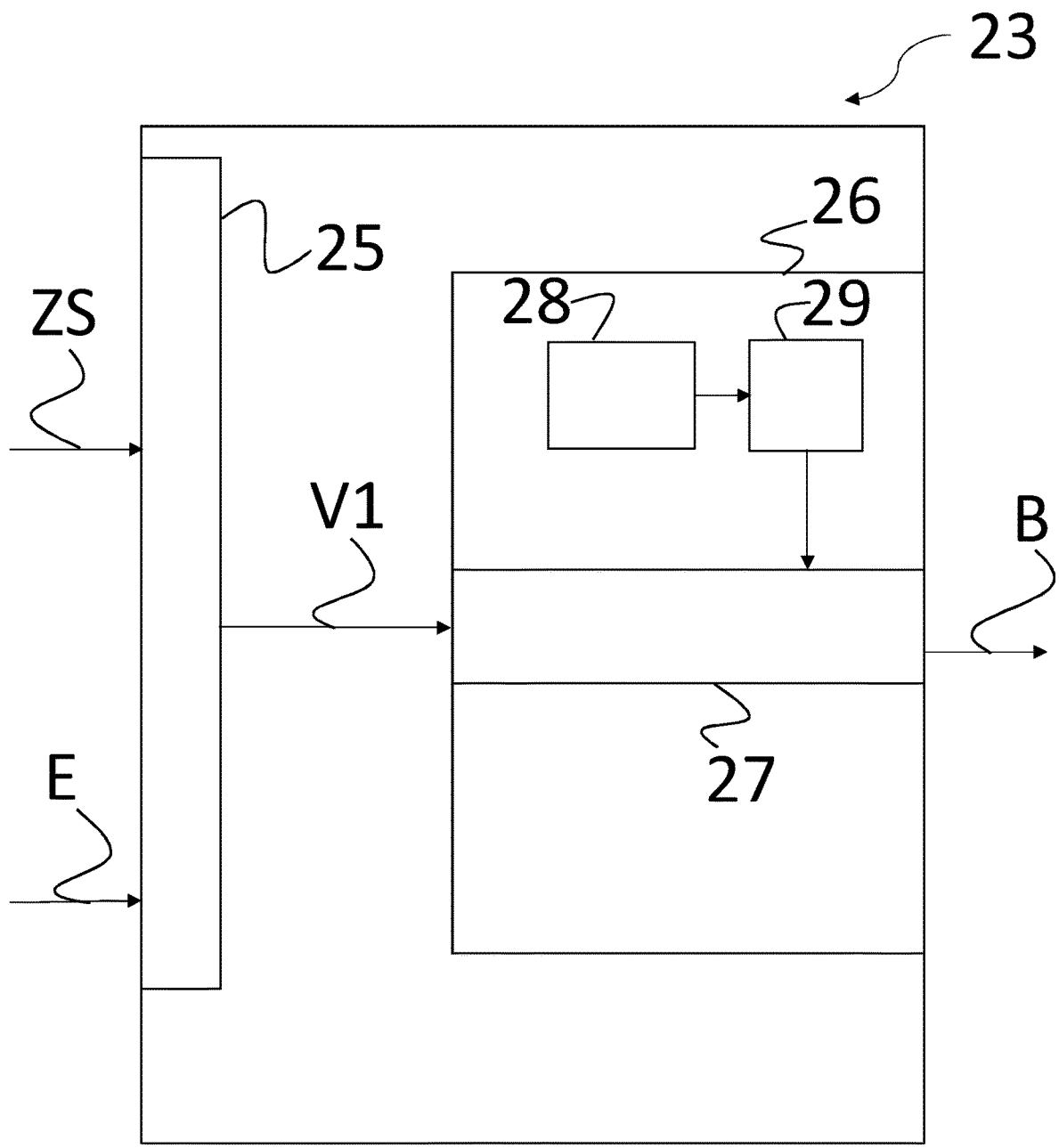
Figure 13:
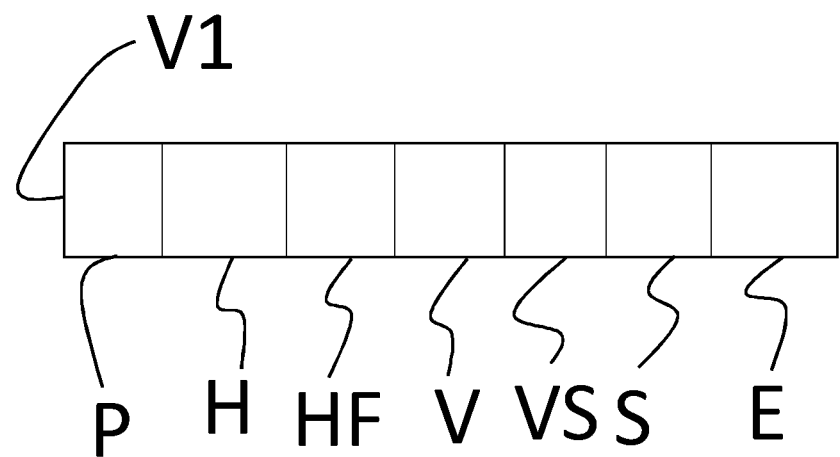
Figure 13:
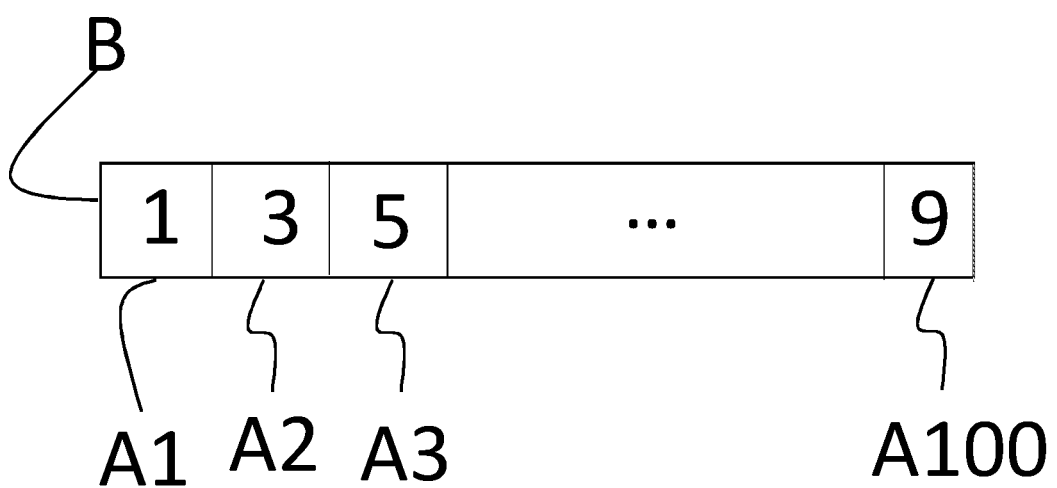
Figure 14:
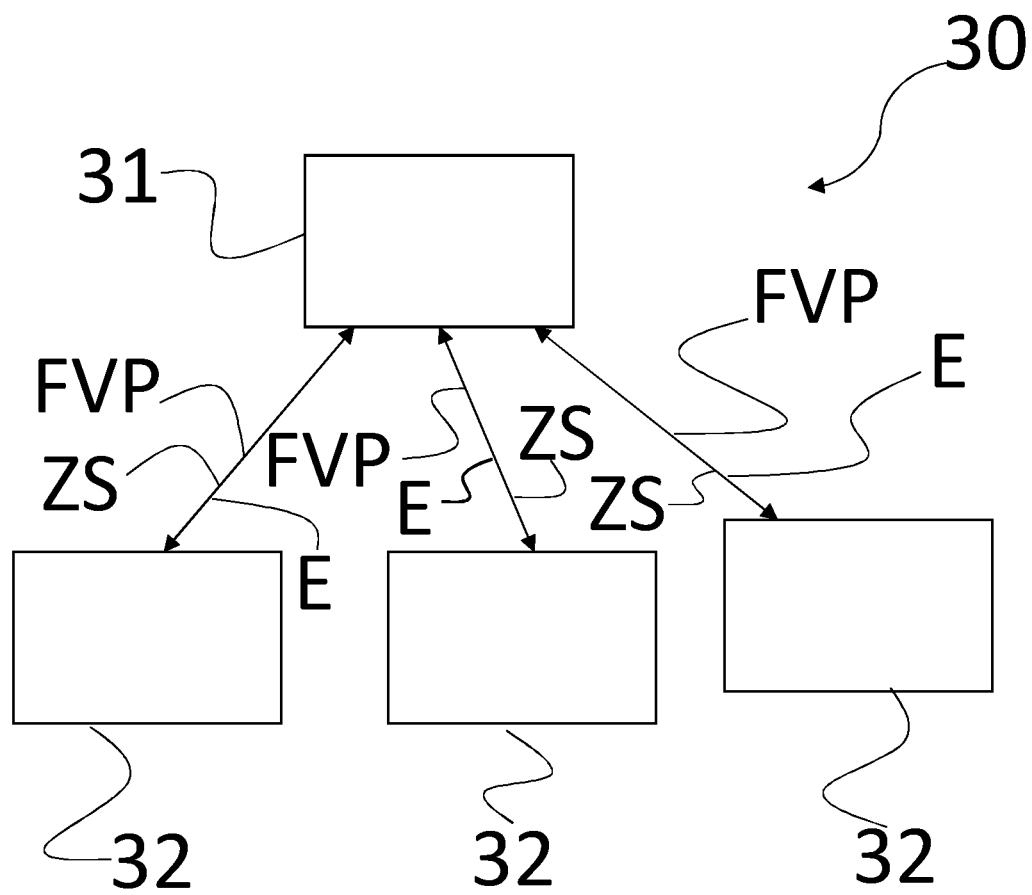

In the figures:

FIG. 1 shows a flow chart, which depicts a method for testing a script according to an embodiment of the invention, FIG. 2 shows a schematic diagram of a visual rating of a script according to an embodiment of the invention, FIG. 3 shows a schematic diagram of a line-by-line rating of a script according to an embodiment of the invention, FIG. 4 shows an exemplary diagram, which quantifies the agreement of a test person, FIG. 5 shows an exemplary diagram, which depicts a reading speed of a test person, FIG. 6 shows a schematic diagram of a rating of a script based on an audio transmission, FIG. 7 shows a schematic diagram of a rating of a film prototype, FIG. 8 shows exemplary diagrams for depicting the relationship between excitement values and physiological measured values, FIG. 9 shows an exemplary diagram for depicting physiological variables measured on test persons during a performance of a preliminary film product, FIG. 10 shows a diagram with excitement values ascertained on the basis of physiological variables shown in FIG. 9, FIG. 11 shows a schematic diagram of a preliminary film product testing device according to an exemplary embodiment of the invention, FIG. 12 shows a schematic diagram of a rating device of a preliminary film product testing device according to an exemplary embodiment of the invention, FIG. 13 shows a schematic diagram of input vectors and rating vectors for an AI-based rating of a preliminary film product according to an exemplary embodiment of the invention, FIG. 14 shows a software kit for realising the inventive method for testing a preliminary film product.

FIG. 1 shows a flow diagram 100, which describes a method for correcting a preliminary film product. In step 1.I initially a treatment T, i.e. a short summary of a film plot is generated as a first written preliminary stage of a script. In the embodiment shown in FIG. 1 this summary is used as the preliminary film product FVP. In step 1.II the content of the treatment T is displayed as text on a display unit such as a screen of a computer. Sections A of the summary are shown separately to each of a plurality of test persons. A section may for example comprise a screen page, but also more than or less than a screen page. The test person can move back and forth in the text by means of a scrolling movement. In other words, the breakdown of the preliminary film product takes places here in connection with the presentation of the text.

In step 1.III after reading a section the test persons each give a rating B by entering rating information. For example they go to one of the (variously hatched) control panels shown in FIG. 2 along the lower edge of the screen in order to enter an estimate of the quality of the section. A dotted hatching (see panel 3*a* in FIG. 2) may mean for example that the person submitting the rating dislikes the section very much. A hatching consisting of vertical lines (see panel 3*b* in FIG. 2) may mean that either the section is still in need of improvement but contains usable ideas, or that the section is not understood sufficiently (enough), and a hatching consisting of horizontal lines (see panel 3*c* in FIG. 2) means that the test person submitting the rating is well pleased with the read section. Instead of hatchings alternative markings can of course be used for the individual control panels, e.g. different colours or similar.

Step 1.IV indicates that the two previous steps 1.II and 1.III keep being repeated until the text is finished. In other words, if the test person has not yet reached the end of the text, he/she is returned to step 1.II. If in step 1.IV the last section of the text was rated, the system goes to step 1.V.

In step 1.V an overall evaluation GA of the plurality of ratings performed by test persons then takes place. This may for example involve weightings being given to the ratings of individual test persons, which are very different. The weightings may for example be ascertained by way of a test phase/learning phase having taken place beforehand with the aid of a mechanical learning procedure. This involves giving a test person a plurality of test scripts to be rated. Thereafter the "quality" of the rating is determined. The "quality" may for example be determined by way of a later actual success of the film relating back to the test script. In other words, if the assessment of the test person matches the assessment of the actual audience, a high quality rating may be assumed. Further clues for a weighting consist in as to whether the test person has a taste similar to that of the target group/has a positive attitude in principle to the subject area of a film.

Based on the section-wise rating of the summary step 1.VI may then be used to make a definite statement on individual sections of a later film product as well as on the overall quality thereof. The likelihood of success of the film product can thus be assessed at an early stage of the film production thereby reducing in this way the risk of an unnecessary input of resources in a film production. Furthermore in step 1.VI corrective measures based on the rating results are performed in order to improve the preliminary film product and thus the chances of success of the later film product.

FIG. 2 shows a schematic diagram of a visual rating of a script according to an exemplary embodiment of the invention. A screen 1 is shown, on which a section of a text of a summary of the film with a plurality of lines 2 is displayed. A test person doing the rating reads the section and then selects with the aid of a mouse one of the three differently coloured panels 3*a*, 3*b*, 3*c* in a rectangular rating panel 3 on the lower edge of the screen in order to supply a rating of the read section. In FIG. 2 the different colours of the individual panels 3*a*, 3*b*, 3*c* are symbolised by different textures. Subsequently the next section is automatically displayed, which again is read by the test person doing the rating. Having read the next section the test person then again supplies a rating etc.

FIG. 3 shows a schematic diagram of a line-by-line rating of a script according to an exemplary embodiment of the invention. Similarly to the embodiment shown in FIG. 2 a section of a summary of a precursor of a script is shown on a screen 1 with a plurality of lines 2, 2*a*, 2*b*. Differently from the embodiment shown in FIG. 2, in the embodiment shown in FIG. 3 individual lines 2*a*, 2*b* are selected and rated by means of a coloured marking. For example the third line 2*a* was marked with a colour, which in FIG. 3 is symbolised by a dotted area 4*a*, and thereby provided with a medium rating, which means that the content shows promising approaches, but could still be improved upon. The fifth line 2*b* by contrast is marked with a white colour bar 4*a*, which means that this line has pleased the rating person very much. With the variant shown in FIG. 3 a summary can be very finely dissolved/rated in a strongly localised manner by braking the sections further down into partial sections (i.e. here into individual lines), so that the authors receive a very precise feedback and can carry out localised corrections to the script more effectively than with a merely section-wise rating (without any further breakdown into partial sections), as it has been realised in the embodiment shown in FIG. 2.

FIG. 4 shows a diagram 5, which represents a rating graph 5a. This shows a value G in dependence of a line index z, which indicates a line number of a section or partial sections. The value G represents, to what extent a section A, a partial section or a sentence has pleased a rating person. After or while still reading the section or after or while reading the entire text the rating person draws a graph, which gives information about which partial sections of the sections have pleased him/her to a greater or lesser extent. The input of the value G may be made for example by a light pen on a tablet or by touching the screen designed as a touchscreen of the tablet with a user finger in a rating panel displayed on the screen for the rating.

FIG. 5 shows a diagram 6, the graph 6a of which was automatically recorded differently from the graph 5a shown in FIG. 4, i.e. while reading through the script. A reading speed V of a reader was determined in dependence of the line/line number z. This reading speed may for example be determined on the basis of a time interval between the ratings of the individual sections or lines. It can also be determined by way of a scrolling speed of the rating person. In order to be able to place a determined graph 6a, an average reading speed Vm can be determined by the rating test person in advance by way of test material. In the sections or lines z, in which the reading speed v of the test person exceeds their average speed Vm, it can be assumed that these sections have especially pleased the reader/that the reader found these sections particularly exciting. By contrast, sections or lines, for which the reader takes a very long time, can be estimated as being uninteresting or boring or difficult to understand. However, this could also mean, as the case may be, exactly the opposite, as already mentioned above. Based on the determined reading speed Vm a rating factor can be ascertained, which indicates the degree of agreement of the reader with a part of a section. With the approach illustrated in FIG. 5 an automated rating is obtained, which can for example be undertaken in addition to an active rating as illustrated in FIG. 2 to FIG. 4, or which can be used as an alternative, if the reader is to be spared active cooperation. This graph can also be created automatically by means of click evaluations.

FIG. 6 shows a scenario 7, where a rating person 8 (test person 8) listens to an audio version of a script via an acoustic playback device 9. The test person 8 can then give acoustic ratings for individual sections by means of corresponding oral inputs. For example, the playback device 9 may comprise a text-to-speech-to-text module, which can convert speech into text and vice-versa. When the text is read out, the user 8 is asked at the end of each section to give oral feedback. The test person 8 specifies for example a value on a scale from 0 to 10. After supplying the spoken number, the system jumps on in order to read the next section. Similarly an oral command may be given for stopping after a single sentence, so that individual sentences just listened to can also be rated. Alternatively or additionally at the end of a paragraph or a single sentence a spoken free text comment can be recorded, with which the respective paragraph/the single sentence is rated. In addition FIG. 6 shows a push button 41, which the test person can actuate in order to give a conscious rating. The test person also carries a pulse sensor 42 on his/her arm, with which state sensor data ZS is acquired, which represents information for a subconscious rating. The state sensor data ZS as well as the conscious rating data E are transmitted to a preliminary film product testing device 20 (for details see FIG. 8), which performs an evaluation on the basis of the recorded data E, ZS and also controls the playback device 9 with the aid of control signals S, in order to synchronise the playback with the rating action of the test person.

FIG. 7 shows a schematic diagram of a playback device 10 of a preliminary film product testing device for a film prototype. The film prototype is shown to the rating test person (not depicted) on a screen 10a of the playback device 10. An acoustic playback then takes place via two loudspeakers 10b arranged on the sides of the screen 10a. The rating test person looks at a scene 11 and, in a rating panel 3 appearing at the lower edge of the screen 10a, selects a coloured panel 3a, 3b, 3c/shown hatched in FIG. 7 for supplying a rating, without having to stop the film. This rating can also be initiated via an external input unit. Alternatively an acoustic rating is possible, similar to the embodiment shown in FIG. 6.

In addition reactions such as eye movements of the test person performing the ratings are pictorially recorded with the aid of a camera 12 arranged on the screen as well as with the aid of a microphone. The recorded eye movements are included in the evaluation of the film prototype. A state of excitement of the rating test person can for example be determined by way of a speed of an eye movement and in this way the effect of the film on the rating test person can be ascertained. Similarly pulse measurements of the rating test person can again be taken during playback of the film prototype and by way of the pulse frequency conclusions can be drawn as to the degree of excitement the rating test person feels (estimates) while watching the film scene. Further values to be measured may include the body temperature and the skin moisture, which can for example be measured via the electrical resistance of the skin.

The measurements of the physiology of the rating test person may for example be evaluated by comparing them to reference values. To this effect the rating test person is shown beforehand reference films, the scenes of which are rated explicitly by the person. At the same time the physiological variables such as eye movement, pulse frequency, body temperature and skin moisture are measured and correlated to the subjective rating of the scenes by the person. In this way a mathematical relationship between the feel of excitement and the recorded physiological variables of the test person can be ascertained, which can then be utilised during rating of the film prototype for evaluation. Finally the different test variables/the partial results connected therewith are again combined to form an overall rating result. Such a combination may for example include a weighted addition of the individual rating variables. The above described approach shall be illustrated in detail with the aid of the following FIGS. 8 to 10.

FIGS. 8 to 10 show diagrams, which depict by way of physiological measurements the above described steps for ascertaining excitement values/values, which represent the feel of excitement of a person. In FIG. 8 physiological measured values such as eye movement Fa, pulse frequency Fp and body temperature Tk are graphically correlated in a diagram with reference values ESR of an excitement feel. The cited values are only examples and shall not imply a restricting meaning. These reference values ESR can for example be recorded once for each test person and stored in a data base.

FIG. 9 graphically shows in a diagram the measured values of the above-said physiological variables of eye movement Fa, pulse frequency Fp and body temperature Tk of a test person in dependence of a line number Z. The measured values Fa, Fp, Tk shown in FIG. 9 are then measured, when a preliminary film product is shown to a test person.

FIG. 10 in a diagram shows both individual excitement graphs ESa, ESp, ESk for the eye movement Fa, the pulse frequency Fp and the body temperature Tk and also a combined excitement graph ESG generated by the addition of the individual excitement graphs and drawn as a dashed line for the graphs of physiological variables recorded in the diagram of FIG. 9.

FIG. 11 schematically shows a preliminary film product testing device 20 according to an embodiment of the invention. The preliminary film product testing device 20 is connected to a playback device 10. The playback device 10 includes a screen (shown in FIGS. 2, 3), on which a preliminary film product can be displayed to a selected circle of test persons, and which comprises a touchscreen function, in order to receive inputs E of a test person.

Die preliminary film product testing device 20 here comprises a structuring unit 21 for breaking the preliminary film product down into individual sections. Structuring signals S are transmitted from the structuring unit 21 to the playback device 10, in order to structure the played-back preliminary film product into individual sections. Part of the preliminary film product testing device 20 is also a recording unit 22 for the section-wise recording of reactions and/or assessments of the test persons during receipt of the preliminary film product by the test persons. The recording unit 22 thus receives input signals E from the playback device 10 as well as state sensor signals ZS from state sensors (not shown), which record the already mentioned state information on the test person. The input signals E recorded by the recording unit 22 and the state sensor signals ZS, which include information on reactions and assessments of the test person, are evaluated by the rating unit 23, wherein a rating B of the individual sections is carried out on the basis of the recorded reactions and/or the assessments of the test persons 8.

The rating data B is transmitted to an overall rating unit 23a, which in the embodiment shown is also part of the preliminary film product testing device 20. The overall rating unit 23a generates an overall result GA by means of a weighted combination of individual ratings B. The weighting may be carried out for example on the basis of consistency values, which were included in the calculation of the ratings and may be part of the rating results B and which allow to give an indication as to whether the subconscious ratings ZS and the conscious inputs E of a test person are consistent. The more consistent this rating information is, the stronger may an individual rating be weighted. There are other factors, which may also be included in the weighting such as for example a value for the competency of the test person or the similarity of the views of the test person with a target group.

Part of the preliminary film product testing device 20 is also a control unit 43, in order to communicate with the individual units 21, 22, 23, 23a of the preliminary film product testing device 20 and to activate the same. The overall rating result is transmitted to a correction unit 24, which is utilised to modify the preliminary film product in dependence of the rating.

FIG. 12 depicts a rating unit 23 of a preliminary film product testing device according to an exemplary embodiment of the invention, as shown for example in FIG. 11. The rating unit 23 comprises a data input interface 25, with which physiological measured values ZS as well as input signals E are received.

The measured values ZS and input signals E are transmitted to an AI rating unit 26 (AI=artificial intelligence). The AI rating unit 26 comprises a neuronal network unit 27, which, on the basis of an input vector V1 of the physiological measured values ZS as well as input signals E, ascertains a rating vector B, which comprises information on a rating of a preliminary film product.

For example, the input vector V1 of the measurements comprises a plurality of measured values, such as for example the reading speed V, the pulse rate P, the skin colour H, skin moisture HF, the speed V of eye movements, the scrolling speed VS, a spectrum S of the acoustic utterings of a test person etc. Such an input vector V1 is shown in FIG. 13. The rating vector B also shown in FIG. 13 comprises for example values for the individual sections A1 . . . A100 or line sections on a scale from 1 to 10, wherein 1 means very negative and 10 means excellent.

Apart from the neuronal network unit 27 the AI rating unit 26 comprises a database 28 and a training unit 29. The neuronal network for the one or more neuronal network units 27 is trained with the aid of the training unit 29. Labeled training data for example may be used in the training process. These include reference data of pairs of input vectors VI and rating vectors B, which e.g. were also generated by way of test films/corresponding preliminary film products using the test persons or the target group. The structures of the neuronal network, such as connections and weightings, were modified in such a way that an associated rating vector B of the reference data is generated by the neuronal network in response to an input vector of the reference data. The trained neuronal network is then used by the neuronal network unit 27 for example for evaluating the emotional measured values of a test person. In other words, the training unit 29 trains by way of a plurality of training data, which comprise realistically ascertained input vectors VI and rating vectors B and are stored in the database 28, a neuronal network, which at the end of the training is transmitted to the neuronal network unit 27, which now on the basis of measured values of the test person generates a rating vector. The database 28 may also be designed as an external database and be connected via a data network to the training unit 29. Equally however, the training unit 29 could also be arranged externally, and the trained neuronal network is handed over to the AI rating unit 26 via a data network for example.

The rating B carried out by the AI rating unit 26, in particular the neuronal network unit 27, may also include a consistency test. This comprises testing as to whether the values of the state signals ZS are consistent with inputs E generated by conscious rating. If for example a state ZS linked to a positive emotion is measured and if the conscious rating E shows a negative attitude, the respective rating of the current section can, as a precaution, be either completely rejected due to its contradictory nature or at least given a weaker weighting.

The rating unit 23 may still include further units, for example a text analysis unit, with which text inputs are analysed with regard to their significance and a quantitative rating variable is generated by way of the significance.

FIG. 14 schematically shows a modular software solution, which can be extended by hardware components. The software 30 includes a server program 31, which is stored on a computer of e.g. a film production company or is stored on cloud. Furthermore the software 30 also includes an app 32, which is stored respectively on the smartphones of the test persons. When a preliminary test product is then to be tested using the method according to the invention, the preliminary test product FVP is transmitted with the aid of the server program 31 to the smartphones of the test persons. The test persons can then view the preliminary test product FVP with the aid of the app 32 or listen to it and generate reactions using corresponding state signals ZS and assessments using corresponding input signals E. The app 32 comprises program parts, with which sensors of the smartphones are activated for recording the reactions and assessments. The app 32 may for example provide a scroll tracking capability. In addition the app 32 uses a camera for recording eye movements or the skin colour of the test person. The camera used for recording the physiology of a test person may for example be a camera integrated in a smartphone. Furthermore the app 32 may also include capabilities for measuring the reading speed, for example on the basis of the eye movements or the scrolling speed/scrolling behaviour. Further the app 32 may comprise a capability for assigning measuring times and/or input times to the recorded reactions and/or assessments. In other words, when measuring a signal ZS connected with a reaction or when recording an input E, which is recorded as part of a transmission of assessment information from the test person to the app 32, the respective points in time of the measurement/input are recorded, and measuring events recorded at the same time or a time very close thereto are assigned to a certain sub-section or a subject of action of a section. The app 32 can also be used to include devices in the test operation, which the test person happens to own and which are equipped with sensors for measuring biometric data. For example, with the aid of the app 32 a sports watch or smart watch can be included in the test operation and used to measure a pulse frequency or skin temperature.

Die app 32 preferably converts the recorded signals into measured values or input texts. The server program 31 receives the measuring values and input texts ascertained by the app 32 as part of the assessments and reactions of the test persons, and conducts an evaluation on the basis of the transmitted information in order to generate rating result data B for the individual sections of the preliminary overview. During the rating the reactions and assessments generated by the individual test persons are combined to form a rating result of the individual sections. The server program 31 also performs further processing steps such as for example the ascertainment of an overall test result as well as a correction of the preliminary overview of the preliminary test product and the film product in order to improve the chances of success of the film production.

Finally it is once more pointed out that the devices described above in detail are merely exemplary embodiments, which may be modified by the expert in many different ways, without departing from the scope of the invention. Furthermore the use of the indefinite article "a" does not exclude that the respective features may also be present several times. Equally the terms "unit" and "module" do not exclude that these may also consist of several, possible also spatially separated sub-units.

LIST OF REFERENCE SYMBOLS 1 playback unit/screen
2, 2a, 2b line
3 rating panel
3a, 3b, 3c hatched partial area
4a, 4b rated lines
5 diagram of a conscious rating
5a "pleased-with" graph
6 diagram of a subconscious rating
6a eye speed graph
6b horizontal straight of an average speed
7 scenario with an acoustic representation of a film material
8 test person/rating person
9 playback unit/audio device
10 playback device
10a screen/touchscreen
10b loudspeaker
11 film scene
12 camera
12a microphone
20 preliminary film product testing device
21 structuring unit
23 rating unit
23a overall rating unit
24 correction unit
25 input interface
26 AI rating unit
27 neuronal network unit
28 database
29 training unit
30 modular software
31 server program
32 app
33 evaluation unit
34 fusion unit
41 push button
42 pulse measuring device
43 control unit
A section
B rating vector
E input signal
ES excitement value
ESa excitement value based on eye movement
ESp excitement value based on heart frequency
ESk excitement value based on body temperature
ESG averaged excitement value
ESR excitement reference value
Fa eye movement
Fh heart frequency
FVP preliminary film product
GA overall result
H skin colour
HF skin moisture
P pulse
S control signal
T treatment
Tk body temperature
V reading speed
Vm average reading speed
V1 input vector
Z line number
ZS state signal

The invention claimed is:

1. A method for testing a preliminary film product (FVP) comprising the steps of:
providing a preliminary film product (FVP) to a selected circle of test persons (8),
dividing the preliminary film product (FVP) into individual sections (A) and section-wise recording of reaction signals (E, ZS) of the test persons (8) during or immediately after receipt of the preliminary film product (FVP) by the test persons (8), the reaction signals including an input signal (E), which is generated by a test person (8) consciously actuating an input interface, and a state sensor signal (ZS), which is generated by recording, by way of sensors, biometric and/or physiological data from a test person (8),
conducting an automatic evaluation of the recorded reaction signals (E, ZS) for generating rating result data (B)

of the individual sections (A), wherein a consistency test takes place between an input signal (E) and a state sensor signal (ZS) assigned to a same sub-section of the section (A) to be assessed, and optionally ascertaining an overall test result (GA) of the preliminary film product (FVP) in dependence of the rating result data (B).

2. The method according to claim 1, wherein in case of a simultaneous or near-simultaneous recording of several different reaction signals (E, ZS) an assignment is made of the different reaction signals (E, ZS) to a common sub-section of the section (A) to be assessed.

3. The method according to claim 1, wherein the preliminary film product (FVP) comprises at least one of the types of playback:
   a text (2),
   an audio version,
   a film presentation (11).

4. The method according to claim 3, wherein the text (2) comprises at least one of the following types of text:
   a synopsis,
   a treatment (T),
   a script.

5. The method according to claim 3, wherein the film presentation (11) comprises at least one of the following types:
   dialogues and/or noises and/or music stored on a graphic story board,
   an animated film,
   a rough cut version of the film product (FP).

6. The method according to claim 1, wherein at least one of the following types of input request signals is generated for creating the input signal (E) by means of a user interface:
   one or more selectable colour bars (3a, 3b, 3c) per section (A) for supplying a rating of the section (A),
   an additional text field for a free text comment,
   a marking (4a, 4b) of individual sentences or semi-sentences of a section (A),
   a field for a graph display (5, 6) for an overall rating of the preliminary overview,
   an acoustic prompt signal.

7. The method according to claim 1, wherein the input signal (E) as acoustic signal, preferably as speech signal, comprises an acoustic recording of
   an oral indication of a scale value,
   and/or
   a free text comment.

8. The method according to claim 1, wherein the state sensor signal (ZS) comprises at least one of the following types of information:
   a pulse value,
   eye movement data,
   measured reading speed data,
   scroll tracking data.

9. A method for correcting a preliminary film product (FVP), including the steps of:
   performing a method according to claim 1,
   correcting the preliminary film product (FVP) in dependence of the rating result data (B) of the performed method.

10. The method according to claim 9, wherein when performing the step of correcting the preliminary film product (FVP) individual sections are modified or discarded, which according to a predefined rating standard have been given an unfavourable rating.

11. The method according to claim 9, wherein modification of a section comprises stipulating a suitable angle of view for the pictorial recording of a section.

12. A preliminary film product testing device (20), comprising:
   one or more processors configured to:
      provide a preliminary film product (FVP) to a selected circle of test persons (8),
      optionally divide the preliminary film product (FVP) into individual sections (A),
      perform section-wise recording of reaction signals (E, ZS) of the test persons (8) during or directly after receipt of the preliminary film product (FVP) by the test persons (8), the reaction signals including an input signal (E), which is generated by a test person (8) consciously actuating an input interface, and a state sensor signal (ZS), which is generated by recording, by way of sensors, biometric and/or physiological data from a test person (8),
      conduct an automatic evaluation of the recorded reaction signals (ZS) for generating rating result data (B) of the individual sections (A), wherein a consistency test takes place between an input signal (E) and a state sensor signal (ZS) assigned to a same sub-section of the section (A) to be assessed, and
      optionally ascertain an overall test result (GA) of the preliminary film product (FVP) in dependence of the rating result data (B).

13. A preliminary film product correction device including:
   a preliminary film product testing device (20) according to claim 12,
   a correcting unit for modifying the preliminary film product (FVP) in dependence of the rating results (B, GA) of the preliminary film product testing device (20) according to claim 12.

14. A non-transitory computer-readable medium storing a computer program product with a computer program, with program sections, in order to execute all steps of the method according to claim 1, when executed by a computer unit.

15. A non-transitory computer-readable medium, on which readable and executable program sections have been stored by a computer unit, in order to execute all steps of the method according to claim 1, when the program sections are executed by the computer unit.

* * * * *